United States Patent
Kane et al.

(10) Patent No.: US 10,709,892 B2
(45) Date of Patent: Jul. 14, 2020

(54) TEMPORAL CONFIGURATION OF A MOTION SENSOR IN AN IMPLANTABLE MEDICAL DEVICE

(71) Applicant: CARDIAC PACEMAKERS, INC., St. Paul, MN (US)

(72) Inventors: Michael J. Kane, St. Paul, MN (US); William J. Linder, Golden Valley, MN (US); Benjamin J. Haasl, Forest Lake, MN (US); Paul Huelskamp, St. Paul, MN (US); Keith R. Maile, New Brighton, MN (US); Ron A. Balczewski, Bloomington, MN (US); Bin Mi, Arden Hills, MN (US); John D. Hatlestad, Maplewood, MN (US); Allan Charles Shuros, St. Paul, MN (US)

(73) Assignee: CARDIAC PACEMAKERS, INC., St. Paul, MN (US)

(*) Notice: Subject to any disclaimer, the term of this patent is extended or adjusted under 35 U.S.C. 154(b) by 166 days.

(21) Appl. No.: 15/935,806

(22) Filed: Mar. 26, 2018

(65) Prior Publication Data
US 2018/0207426 A1    Jul. 26, 2018

Related U.S. Application Data

(62) Division of application No. 15/243,524, filed on Aug. 22, 2016, now Pat. No. 9,956,414.
(Continued)

(51) Int. Cl.
*A61N 1/365* (2006.01)
*A61N 1/37* (2006.01)
(Continued)

(52) U.S. Cl.
CPC ........ *A61N 1/36542* (2013.01); *A61B 5/0452* (2013.01); *A61B 5/1118* (2013.01);
(Continued)

(58) Field of Classification Search
None
See application file for complete search history.

(56) References Cited

U.S. PATENT DOCUMENTS 3,835,864 A    9/1974  Rasor et al.
3,943,936 A    3/1976  Rasor et al.
(Continued)

FOREIGN PATENT DOCUMENTS

AU    2008279789 B2    10/2011
AU    2008329620 B2    5/2014
(Continued)

OTHER PUBLICATIONS

US 8,886,318 B2, 11/2014, Jacobson et al. (withdrawn)
(Continued)

*Primary Examiner* — Brian T Gedeon
(74) *Attorney, Agent, or Firm* — Seager, Tufte & Wickhem LLP

(57) ABSTRACT

Methods and devices for configuring the use of a motion sensor in an implantable cardiac device. The electrical signals of the patient's heart are observed and may be correlated to the physical motion of the heart as detected by the motion sensor of the implantable cardiac device in order to facilitate temporal configuration of motion sensor data collection that avoids detecting cardiac motion in favor of overall motion of the patient.

19 Claims, 12 Drawing Sheets

Related U.S. Application Data

(60) Provisional application No. 62/210,882, filed on Aug. 27, 2015.

(51) Int. Cl.
*A61B 5/11* (2006.01)
*A61B 5/00* (2006.01)
*A61N 1/368* (2006.01)
*A61N 1/375* (2006.01)
*A61B 5/0452* (2006.01)
*A61N 1/372* (2006.01)

(52) U.S. Cl.
CPC ............ *A61B 5/686* (2013.01); *A61B 5/6869* (2013.01); *A61N 1/3684* (2013.01); *A61N 1/371* (2013.01); *A61N 1/3756* (2013.01); *A61B 5/1107* (2013.01); *A61B 2562/0219* (2013.01); *A61N 1/36578* (2013.01); *A61N 1/37205* (2013.01)

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Kludziak et al. |
| 4,476,868 A | 10/1984 | Thompson |
| 4,522,208 A | 6/1985 | Buffet |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,466,246 A | 11/1995 | Silvian |
| 5,468,254 A | 11/1995 | Hahn et al. |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,591,214 A | 1/1997 | Lu |
| 5,620,466 A | 4/1997 | Haefner et al. |
| 5,634,938 A | 6/1997 | Swanson et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,954,757 A | 9/1999 | Gray |
| 5,978,713 A | 11/1999 | Prutchi et al. |
| 5,991,660 A | 11/1999 | Goyal |
| 5,999,848 A | 12/1999 | Gord et al. |
| 5,999,857 A | 12/1999 | Weijand et al. |
| 6,026,320 A | 2/2000 | Carlson et al. |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,141,581 A | 10/2000 | Olson et al. |
| 6,141,588 A | 10/2000 | Cox et al. |

(56) References Cited

U.S. PATENT DOCUMENTS

| | | |
|---|---|---|
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,298,271 B1 | 10/2001 | Weijand |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,110,824 B2 | 9/2006 | Amundson et al. |
| 7,120,504 B2 | 10/2006 | Osypka |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,790 B2 | 4/2007 | Thompson et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |

(56) References Cited

U.S. PATENT DOCUMENTS

| | | |
|---|---|---|
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,778,699 B1 | 8/2010 | Ferrise et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |

(56) References Cited

U.S. PATENT DOCUMENTS

| | | | |
|---|---|---|---|
| 8,224,244 | B2 | 7/2012 | Kim et al. |
| 8,233,985 | B2 | 7/2012 | Bulkes et al. |
| 8,265,748 | B2 | 9/2012 | Liu et al. |
| 8,265,757 | B2 | 9/2012 | Mass et al. |
| 8,280,521 | B2 | 10/2012 | Haubrich et al. |
| 8,285,387 | B2 | 10/2012 | Utsi et al. |
| 8,290,598 | B2 | 10/2012 | Boon et al. |
| 8,290,600 | B2 | 10/2012 | Hastings et al. |
| 8,295,939 | B2 | 10/2012 | Jacobson |
| 8,301,254 | B2 | 10/2012 | Mosesov et al. |
| 8,315,701 | B2 | 11/2012 | Cowan et al. |
| 8,315,708 | B2 | 11/2012 | Berthelsdorf et al. |
| 8,321,021 | B2 | 11/2012 | Kisker et al. |
| 8,321,036 | B2 | 11/2012 | Brockway et al. |
| 8,332,036 | B2 | 12/2012 | Hastings et al. |
| 8,335,563 | B2 | 12/2012 | Stessman |
| 8,335,568 | B2 | 12/2012 | Heruth et al. |
| 8,340,750 | B2 | 12/2012 | Prakash et al. |
| 8,340,780 | B2 | 12/2012 | Hastings et al. |
| 8,352,025 | B2 | 1/2013 | Jacobson |
| 8,352,028 | B2 | 1/2013 | Wenger |
| 8,352,038 | B2 | 1/2013 | Mao et al. |
| 8,359,098 | B2 | 1/2013 | Lund et al. |
| 8,364,276 | B2 | 1/2013 | Willis |
| 8,369,959 | B2 | 2/2013 | Meskens |
| 8,369,962 | B2 | 2/2013 | Abrahamson |
| 8,380,320 | B2 | 2/2013 | Spital |
| 8,386,051 | B2 | 2/2013 | Rys |
| 8,391,981 | B2 | 3/2013 | Mosesov |
| 8,391,990 | B2 | 3/2013 | Smith et al. |
| 8,406,874 | B2 | 3/2013 | Liu et al. |
| 8,406,886 | B2 | 3/2013 | Gaunt et al. |
| 8,412,352 | B2 | 4/2013 | Griswold et al. |
| 8,417,340 | B2 | 4/2013 | Goossen |
| 8,417,341 | B2 | 4/2013 | Freeberg |
| 8,423,149 | B2 | 4/2013 | Hennig |
| 8,428,722 | B2 | 4/2013 | Verhoef et al. |
| 8,433,402 | B2 | 4/2013 | Ruben et al. |
| 8,433,409 | B2 | 4/2013 | Johnson et al. |
| 8,433,420 | B2 | 4/2013 | Bange et al. |
| 8,447,412 | B2 | 5/2013 | Dal Molin et al. |
| 8,452,413 | B2 | 5/2013 | Young et al. |
| 8,457,740 | B2 | 6/2013 | Osche |
| 8,457,742 | B2 | 6/2013 | Jacobson |
| 8,457,761 | B2 | 6/2013 | Wariar |
| 8,478,407 | B2 | 7/2013 | Demmer et al. |
| 8,478,408 | B2 | 7/2013 | Hastings et al. |
| 8,478,431 | B2 | 7/2013 | Griswold et al. |
| 8,504,156 | B2 | 8/2013 | Bonner et al. |
| 8,509,910 | B2 | 8/2013 | Sowder et al. |
| 8,515,559 | B2 | 8/2013 | Roberts et al. |
| 8,527,068 | B2 | 9/2013 | Ostroff |
| 8,532,790 | B2 | 9/2013 | Griswold |
| 8,541,131 | B2 | 9/2013 | Lund et al. |
| 8,543,205 | B2 | 9/2013 | Ostroff |
| 8,547,248 | B2 | 10/2013 | Zdeblick et al. |
| 8,548,605 | B2 | 10/2013 | Ollivier |
| 8,554,333 | B2 | 10/2013 | Wu et al. |
| 8,565,878 | B2 | 10/2013 | Allavatam et al. |
| 8,565,882 | B2 | 10/2013 | Mates |
| 8,565,897 | B2 | 10/2013 | Regnier et al. |
| 8,571,678 | B2 | 10/2013 | Wang |
| 8,577,327 | B2 | 11/2013 | Makdissi et al. |
| 8,588,926 | B2 | 11/2013 | Moore et al. |
| 8,612,002 | B2 | 12/2013 | Faltys et al. |
| 8,615,310 | B2 | 12/2013 | Khairkhahan et al. |
| 8,626,294 | B2 | 1/2014 | Sheldon et al. |
| 8,634,908 | B2 | 1/2014 | Cowan |
| 8,634,912 | B2 | 1/2014 | Bornzin et al. |
| 8,634,919 | B1 | 1/2014 | Hou et al. |
| 8,639,335 | B2 | 1/2014 | Peichel et al. |
| 8,644,934 | B2 | 2/2014 | Hastings et al. |
| 8,649,859 | B2 | 2/2014 | Smith et al. |
| 8,670,842 | B1 | 3/2014 | Bornzin et al. |
| 8,676,319 | B2 | 3/2014 | Knoll |
| 8,676,335 | B2 | 3/2014 | Katoozi et al. |
| 8,700,173 | B2 | 4/2014 | Edlund |
| 8,700,181 | B2 | 4/2014 | Bornzin et al. |
| 8,705,599 | B2 | 4/2014 | dal Molin et al. |
| 8,718,773 | B2 | 5/2014 | Willis et al. |
| 8,738,147 | B2 | 5/2014 | Hastings et al. |
| 8,744,572 | B1 | 6/2014 | Greenhut et al. |
| 8,747,314 | B2 | 6/2014 | Stahmann et al. |
| 8,755,884 | B2 | 6/2014 | Demmer et al. |
| 8,758,365 | B2 | 6/2014 | Bonner et al. |
| 8,774,572 | B2 | 7/2014 | Hamamoto |
| 8,781,605 | B2 | 7/2014 | Bornzin et al. |
| 8,788,035 | B2 | 7/2014 | Jacobson |
| 8,788,053 | B2 | 7/2014 | Jacobson |
| 8,798,740 | B2 | 8/2014 | Samade et al. |
| 8,798,745 | B2 | 8/2014 | Jacobson |
| 8,798,762 | B2 | 8/2014 | Fain et al. |
| 8,798,770 | B2 | 8/2014 | Reddy |
| 8,805,505 | B1 | 8/2014 | Roberts |
| 8,805,528 | B2 | 8/2014 | Corndorf |
| 8,812,109 | B2 | 8/2014 | Blomqvist et al. |
| 8,818,504 | B2 | 8/2014 | Bodner et al. |
| 8,831,747 | B1 | 9/2014 | Min et al. |
| 8,855,789 | B2 | 10/2014 | Jacobson |
| 8,868,186 | B2 | 10/2014 | Kroll |
| 8,886,339 | B2 | 11/2014 | Faltys et al. |
| 8,903,500 | B2 | 12/2014 | Smith et al. |
| 8,903,513 | B2 | 12/2014 | Ollivier |
| 8,914,131 | B2 | 12/2014 | Bornzin et al. |
| 8,923,795 | B2 | 12/2014 | Makdissi et al. |
| 8,923,963 | B2 | 12/2014 | Bonner et al. |
| 8,938,300 | B2 | 1/2015 | Rosero |
| 8,942,806 | B2 | 1/2015 | Sheldon et al. |
| 8,958,892 | B2 | 2/2015 | Khairkhahan et al. |
| 8,977,358 | B2 | 3/2015 | Ewert et al. |
| 8,989,873 | B2 | 3/2015 | Locsin |
| 8,996,109 | B2 | 3/2015 | Karst et al. |
| 9,002,467 | B2 | 4/2015 | Smith et al. |
| 9,008,776 | B2 | 4/2015 | Cowan et al. |
| 9,008,777 | B2 | 4/2015 | Dianaty et al. |
| 9,014,818 | B2 | 4/2015 | Deterre et al. |
| 9,017,341 | B2 | 4/2015 | Bornzin et al. |
| 9,020,611 | B2 | 4/2015 | Khairkhahan et al. |
| 9,037,262 | B2 | 5/2015 | Regnier et al. |
| 9,042,984 | B2 | 5/2015 | Demmer et al. |
| 9,072,911 | B2 | 7/2015 | Hastings et al. |
| 9,072,913 | B2 | 7/2015 | Jacobson |
| 9,155,882 | B2 | 10/2015 | Grubac et al. |
| 9,168,372 | B2 | 10/2015 | Fain |
| 9,168,380 | B1 | 10/2015 | Greenhut et al. |
| 9,168,383 | B2 | 10/2015 | Jacobson et al. |
| 9,180,285 | B2 | 11/2015 | Moore et al. |
| 9,192,774 | B2 | 11/2015 | Jacobson |
| 9,205,225 | B2 | 12/2015 | Khairkhahan et al. |
| 9,216,285 | B1 | 12/2015 | Boling et al. |
| 9,216,293 | B2 | 12/2015 | Berthiaume et al. |
| 9,216,298 | B2 | 12/2015 | Jacobson |
| 9,227,077 | B2 | 1/2016 | Jacobson |
| 9,238,145 | B2 | 1/2016 | Wenzel et al. |
| 9,242,102 | B2 | 1/2016 | Khairkhahan et al. |
| 9,242,113 | B2 | 1/2016 | Smith et al. |
| 9,248,300 | B2 | 2/2016 | Rys et al. |
| 9,265,436 | B2 | 2/2016 | Min et al. |
| 9,265,962 | B2 | 2/2016 | Dianaty et al. |
| 9,272,155 | B2 | 3/2016 | Ostroff |
| 9,278,218 | B2 | 3/2016 | Karst et al. |
| 9,278,229 | B1 | 3/2016 | Reinke et al. |
| 9,283,381 | B2 | 3/2016 | Grubac et al. |
| 9,283,382 | B2 | 3/2016 | Berthiaume et al. |
| 9,289,612 | B1 | 3/2016 | Sambelashvili et al. |
| 9,302,115 | B2 | 4/2016 | Molin et al. |
| 9,333,364 | B2 | 5/2016 | Echt et al. |
| 9,358,387 | B2 | 6/2016 | Suwito et al. |
| 9,358,400 | B2 | 6/2016 | Jacobson |
| 9,364,675 | B2 | 6/2016 | Deterre et al. |
| 9,370,663 | B2 | 6/2016 | Moulder |
| 9,375,580 | B2 | 6/2016 | Bonner et al. |
| 9,375,581 | B2 | 6/2016 | Baru et al. |
| 9,381,365 | B2 | 7/2016 | Kibler et al. |

(56) References Cited

U.S. PATENT DOCUMENTS

| | | |
|---|---|---|
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,517,017 B2 * | 12/2016 | Shuros .................... A61B 5/02 |
| 9,814,406 B2 * | 11/2017 | Razavi ................ A61B 5/0468 |
| 9,956,414 B2 | 5/2018 | Kane et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0041866 A1 | 3/2003 | Linberg et al. |
| 2003/0088278 A1 | 5/2003 | Bardy et al. |
| 2003/0097153 A1 | 5/2003 | Bardy et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Arx et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0118054 A1 | 5/2007 | Pinhas et al. |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255327 A1 | 11/2007 | Cho et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |

(56) References Cited

U.S. PATENT DOCUMENTS

| | | |
|---|---|---|
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204170 A1 | 8/2009 | Hastings et al. |
| 2009/0210024 A1 | 8/2009 | Brooke |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0078322 A1 | 3/2012 | Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |

(56) References Cited

U.S. PATENT DOCUMENTS

| | | |
|---|---|---|
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0257324 A1 | 9/2014 | Fain |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0051823 A1 | 2/2016 | Maile et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0256694 A1 | 9/2016 | Shuros et al. |
| 2017/0056665 A1 | 3/2017 | Kane et al. |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 2662113 A3 | 11/2013 |
| EP | 1948296 B1 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004102105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 1/2005 |
| WO | 2005042089 A1 | 5/2005 |
| WO | 2006086435 A3 | 8/2006 |
| WO | 2006113659 A1 | 10/2006 |
| WO | 2006124833 A3 | 11/2006 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 7/2013 |
| WO | 2013184787 A1 | 12/2013 |

OTHER PUBLICATIONS

"Instructions for Use System 1, Leadless Cardiac Pacemaker (LCP) and Delivery Catheter," Nanostim Leadless Pacemakers, pp. 1-28, 2013.

Hachisuka et al., "Development and Performance Analysis of an Intra-Body Communication Device," The 12th ntemational Conference on Solid State Sensors, Actuators and Microsystems, vol. 4A1.3, pp. 1722-1725, 2003.

International Search Report and Written Opinion dated Feb. 6, 2017 for International Application No. PCT/US2016/048353.

(56) References Cited

OTHER PUBLICATIONS

Invitation to Pay Additional Fees and, Where Applicable, Protest Fee, dated Dec. 9, 2016.
Wegmüller, "Intra-Body Communication for Biomedical Sensor Networks," Diss. ETH, No. 17323, 1-173, 2007.
Notification of Transmittal of the International Search Report and the Written Opinion of the International Searching Authority, or the Declaration, dated Jan. 29, 2016, 15 pages.
Seyedi et al., "A Survey on Intrabody Communications for Body Area Network Application," IEEE Transactions on Biomedical Engineering, vol. 60(8): 2067-2079, 2013.
Spickler et al., "Totally Self-Contained Intracardiac Pacemaker," Journal of Electrocardiology, vol. 3(3&4): 324-331, 1970.

* cited by examiner

TEMPORAL CONFIGURATION OF A MOTION SENSOR IN AN IMPLANTABLE MEDICAL DEVICE

CROSS REFERENCE TO RELATED APPLICATIONS

The present application is a divisional of U.S. patent application Ser. No. 15/243,524, filed Aug. 22, 2016, which claims the benefit of and priority to U.S. Provisional Patent Application Ser. No. 62/210,882, filed Aug. 27, 2015, the disclosures of which are incorporated herein by reference.

TECHNICAL FIELD

The present disclosure generally relates to systems, devices, and methods for treating medical conditions using an implantable device, and more particularly, to systems, devices, and methods which include or use a motion sensor to detect a patient's level of activity.

BACKGROUND

Pacing instruments can be used to treat patients suffering from various heart conditions that result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) have been implanted in a patient's body. Such devices may monitor and provide electrical stimulation to the heart to help the heart operate in a more normal, efficient and/or safe manner. In some cases, a patient may have multiple implanted devices.

Motion detectors have been used in some pacemakers and other implantable devices to obtain a measure of the activity level of the patient. For example, rate adaptive cardiac pacemakers may adjust the rate at which the patient's heart is paced up or down in response to detected motion of the patient. By so doing, the pacemaker is able to adapt to the activity level of the patient, allowing a more active lifestyle than could be achieved without rate adaptive pacing. New and alternative approaches to the use of motion sensors are desired.

OVERVIEW

In some embodiments the present invention relates to a leadless cardiac pacemaker (LCP) or other implantable cardiac device having a motion sensor for detecting motion of the patient. The standard implant for pacemakers has long been the transvenous pacemaker, having a canister housing operational circuitry typically implanted in the upper chest of the patient and a lead which traverses the vasculature to the interior of the heart, with electrodes attached to the heart to facilitate therapy delivery and cardiac signal sensing. Such devices included a motion sensor in the canister, placed outside the ribs on the patient's chest in most examples.

For certain newer generation devices including the LCP, the entire product, including the motion sensor, may be placed inside or in close proximity to the heart. However, such placement means that the motion sensor may detect motion of the heart when it beats in addition to motion caused by bodily movement of the patient. In several embodiments the present invention is directed toward methods and devices that use the temporal patterns of cardiac movement to avoid detecting cardiac motion in place of bodily motion.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This disclosure describes systems, devices, and methods for delivering electrical stimulation to a heart in a rate adaptive manner. Healthy people's bodies generally adjust the rate at which their hearts beat in response to higher or lower metabolic needs, for example during exercise or in response to various external stimuli. However, some people develop diseases or conditions which affect their bodies' abilities to cause their hearts to contract in an effective manner. Accordingly, devices in accordance with the present disclosure may be implanted in such people. In some instances, the implanted devices may deliver electrical stimulation on an on-going basis and adjust the rate of delivered electrical stimulation in accordance with sensed physiological parameters indicative of increased metabolic needs.

Figure 1:
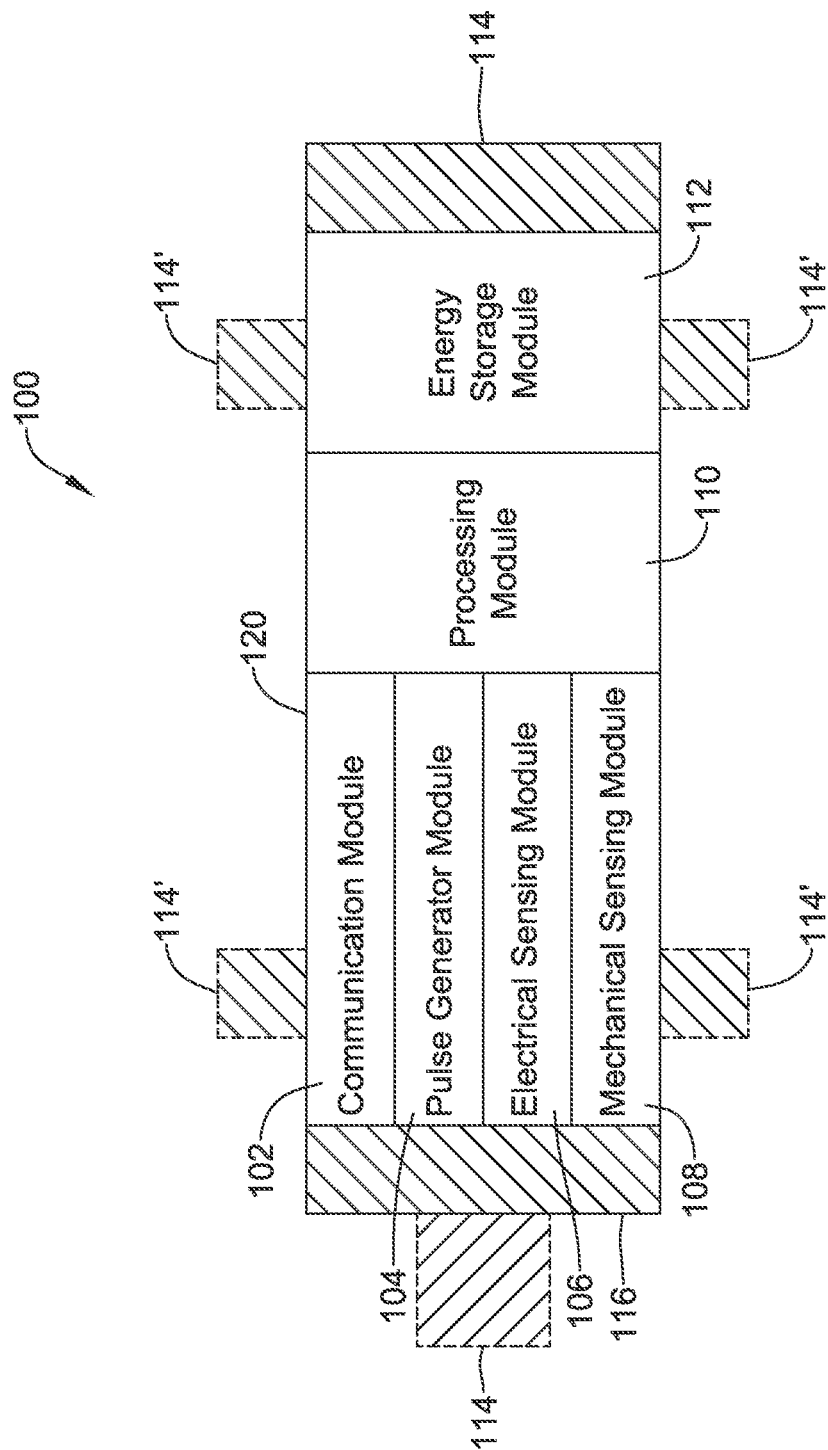
FIG. 1 is a schematic block diagram of an illustrative leadless cardiac pacemaker (LCP) according to one illustrative embodiment of the present disclosure.

FIG. 1 is similar to FIG. 1 of commonly assigned U.S. Provisional Patent Application 62/128,340, the disclosure of which is incorporated herein by reference as showing and describing numerous additional details which may be included in the methods, systems and devices discussed herein.

More specifically, FIG. 1 is a conceptual schematic block diagram of an exemplary leadless cardiac pacemaker (LCP) that may be implanted on the heart or within a chamber of the heart and may operate to sense physiological signals and parameters and deliver one or more types of electrical stimulation therapy to the heart of the patient. Example electrical stimulation therapy may include bradycardia pacing, rate responsive pacing therapy, cardiac resynchronization therapy (CRT), anti-tachycardia pacing (ATP) therapy and/or the like. As can be seen in FIG. 1, LCP 100 may be a compact device with all components housed within LCP 100 or directly on housing 120. In some instances, LCP 100 may include communication module 102, pulse generator module 104, electrical sensing module 106, mechanical sensing module 108, processing module 110, energy storage module 112, and electrodes 114. In some examples (not shown), an optional lead or tether may be attached to an implantable device similar to LCP 100 to provide an additional electrode, extended antenna functionality, to couple to a second such implantable device, or to prevent migration.

As depicted in FIG. 1, LCP 100 may include electrodes 114, which can be secured relative to housing 120 and electrically exposed to tissue and/or blood surrounding LCP 100. Electrodes 114 may generally conduct electrical signals to and from LCP 100 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by the cardiac electrogram (EGM), if observed on or in the heart, or the electrocardiogram (ECG), if observed at some distance from the heart.

Electrodes 114 may include one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In embodiments where electrodes 114 are secured directly to housing 120, an insulating material may electrically isolate the electrodes 114 from adjacent electrodes, housing 120, and/or other parts of LCP 100. In some instances, some or all of electrodes 114 may be spaced from housing 120 and connected to housing 120 and/or other components of LCP 100 through connecting wires. In such instances, the electrodes 114 may be placed on a tail (not shown) that extends out away from the housing 120. As shown in FIG. 1, in some embodiments, LCP 100 may include electrodes 114'. Electrodes 114' may be in addition to electrodes 114, or may replace one or more of electrodes 114. Electrodes 114' may be similar to electrodes 114 except that electrodes 114' are disposed on the sides of LCP 100. In some cases, electrodes 114' may increase the number of electrodes by which LCP 100 may deliver communication signals and/or electrical stimulation pulses, and/or may sense intrinsic cardiac electrical signals, communication signals, and/or electrical stimulation pulses. Electrodes 114 and/or 114' may assume any of a variety of sizes and/or shapes, and may be spaced at any of a variety of spacings. For example, electrodes 114 may have an outer diameter of two to twenty millimeters (mm). In other embodiments, electrodes 114 and/or 114' may have a diameter of two, three, five, seven millimeters (mm), or any other suitable diameter, dimension and/or shape. Example lengths for electrodes 114 and/or 114' may include, for example, one, three, five, ten millimeters (mm), or any other suitable length. As used herein, the length is a dimension of electrodes 114 and/or 114' that extends away from the outer surface of the housing 120. In some instances, at least some of electrodes 114 and/or 114' may be spaced from one another by a distance of twenty, thirty, forty, fifty millimeters (mm), or any other suitable spacing. The electrodes 114 and/or 114' of a single device may have different sizes with respect to each other, and the spacing and/or lengths of the electrodes on the device may or may not be uniform.

In the embodiment shown, communication module 102 may be electrically coupled to electrodes 114 and/or 114' and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. Communication module 102 may additionally be configured to sense for communication signals delivered by other devices, which may be located external or internal to the patient's body.

Communication module 102 may communicate to help accomplish one or more desired functions. Some example functions include delivering sensed data, using communicated data for determining occurrences of events such as arrhythmias, coordinating delivery of electrical stimulation therapy, and/or other functions. In some cases, LCP 100 may use communication signals to communicate raw information, processed information, messages and/or commands, and/or other data. Raw information may include information such as sensed electrical signals (e.g. a sensed EGM), signals gathered from coupled sensors, and the like. In some embodiments, the processed information may include signals that have been filtered using one or more signal processing techniques. Processed information may also include parameters and/or events that are determined by the LCP 100 and/or another device, such as a determined heart rate, timing of determined heartbeats, timing of other determined events, determinations of threshold crossings, expirations of monitored time periods, activity level parameters, blood-oxygen parameters, blood pressure parameters, heart sound parameters, and the like. Messages and/or commands may include instructions or the like directing another device to take action, notifications of imminent actions of the sending device, requests for reading from the receiving device, requests for writing data to the receiving device, information messages, and/or other messages commands.

In at least some embodiments, communication module 102 (or LCP 100) may further include switching circuitry to selectively connect one or more of electrodes 114 and/or 114' to communication module 102 in order to select which electrodes 114 and/or 114' that communication module 102 delivers communication pulses. It is contemplated that communication module 102 may be communicating with other devices via conducted signals, radio frequency (RF) signals, optical signals, acoustic signals, inductive coupling, and/or any other suitable communication methodology. Where communication module 102 generates electrical communication signals, communication module 102 may include one or more capacitor elements and/or other charge storage devices to aid in generating and delivering communication signals. In the embodiment shown, communication module 102 may use energy stored in energy storage module 112 to generate the communication signals. In at least some examples, communication module 102 may include a switching circuit that is connected to energy storage module 112 and, with the switching circuitry, may connect energy storage module 112 to one or more of electrodes 114/114' to generate the communication signals.

As shown in FIG. 1, a pulse generator module 104 may be electrically connected to one or more of electrodes 114 and/or 114'. Pulse generator module 104 may be configured to generate electrical stimulation pulses and deliver the electrical stimulation pulses to tissues of a patient via one or more of the electrodes 114 and/or 114' to provide electrical stimulation therapies such as bradycardia pacing, ATP, CRT, cardioversion or defibrillation.

The LCP 100 may vary the rate at which pulse generator 104 generates the electrical stimulation pulses, for example in rate adaptive pacing. These are just some examples. When used to treat other ailments, the pulse generator module 104 may generate electrical stimulation pulses suitable for neurostimulation or neuromodulation therapy or the like.

Pulse generator module 104 may include one or more capacitor elements and/or other charge storage devices to aid in generating and delivering appropriate electrical stimulation pulses. In the embodiment shown, pulse generator module 104 may use energy stored in energy storage module 112 to generate the electrical stimulation pulses. In some examples, pulse generator module 104 may include a switching circuit that is connected to energy storage module 112 and may connect energy storage module 112 to one or more of electrodes 114/114' to generate electrical stimulation pulses.

Pulse generator module 104 may include the capability to modify the electrical stimulation pulses, such as by adjusting the pulse width and/or amplitude of the electrical stimulation pulses. When pacing the heart, this may help tailor the electrical stimulation pulses to capture the heart a particular patient, sometimes with reduced battery usage. For neurostimulation therapy, adjusting the pulse width and/or amplitude may help tailor the therapy for a particular application and/or help make the therapy more effective for a particular patient.

In some embodiments, LCP 100 may include an electrical sensing module 106 and mechanical sensing module 108. Electrical sensing module 106 may be configured to sense intrinsic cardiac electrical signals conducted from electrodes 114 and/or 114' to electrical sensing module 106. For example, electrical sensing module 106 may be electrically connected to one or more electrodes 114 and/or 114' and electrical sensing module 106 may be configured to receive cardiac electrical signals conducted through electrodes 114 and/or 114' via a sensor amplifier or the like. In some embodiments, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals.

Mechanical sensing module 108 may include, or be electrically connected to, various sensors, such as accelerometers, blood pressure sensors, heart sound sensors, piezoelectric sensors, blood-oxygen sensors, and/or other sensors which measure one or more physiological parameters of the heart and/or patient. Mechanical sensing module 108 may gather signals from the sensors indicative of the various physiological parameters. Both electrical sensing module 106 and mechanical sensing module 108 may be connected to processing module 110 and may provide signals representative of the sensed cardiac electrical signals and/or physiological signals to processing module 110. Although described with respect to FIG. 1 as separate sensing modules, in some embodiments, electrical sensing module 106 and mechanical sensing module 108 may be combined into a single module. In at least some examples, LCP 100 may only include one of electrical sensing module 106 and mechanical sensing module 108. In some cases, any combination of the processing module 110, electrical sensing module 106, mechanical sensing module 108, communication module 102, pulse generator module 104 and/or energy storage module may be considered a controller of the LCP 100.

The mechanical sensing module may include, for example, a micro-electro-mechanical system (MEMS) based motion sensor. This may include a 1, 2 or 3 dimensional motion sensor and may take any of numerous forms known in the art. Some examples may include a micro-machine size vibrating element that varies an electrical parameter when motion impacts it. To facilitate sensing, the motion sensor can be turned "on," requiring current drain, and the output can then be sampled to generate an output. Keeping the motion sensor "on" all the time may drain battery sourced current unnecessarily, and so duty cycling is performed to minimize current draw in some embodiments.

Processing module 110 may be configured to direct the operation of LCP 100. For example, processing module 110 may be configured to receive cardiac electrical signals from electrical sensing module 106 and/or physiological signals from mechanical sensing module 108. Based on the received signals, processing module 110 may determine, for example, occurrences and types of arrhythmias. Processing module 110 may further receive information from communication module 102. In some embodiments, processing module 110 may additionally use such received information to determine occurrences and types of arrhythmias. However, in other embodiments, LCP 100 may use the received information instead of the signals received from electrical sensing module 106 and/or mechanical sensing module 108—for instance if the received information is deemed to be more accurate than the signals received from electrical sensing module 106 and/or mechanical sensing module 108 or if electrical sensing module 106 and/or mechanical sensing module 108 have been disabled or omitted from LCP 100.

After determining therapy is needed, processing module 110 may control pulse generator module 104 to generate electrical stimulation pulses in accordance with one or more electrical stimulation therapy regimens. For example, processing module 110 may control pulse generator module 104 to generate pacing pulses with varying parameters and in different sequences to effectuate one or more electrical stimulation therapies. As one example, in controlling pulse generator module 104 to deliver bradycardia pacing therapy, processing module 110 may control pulse generator module 104 to deliver pacing pulses designed to capture the heart of the patient at a regular interval to help prevent the heart of a patient from falling below a predetermined threshold.

In some embodiments, processing module 110 may further control communication module 102 to send information to other devices. For example, processing module 110 may control communication module 102 to generate one or more communication signals for communicating with other devices of a system of devices. For instance, processing module 110 may control communication module 102 to generate communication signals in particular pulse sequences, where the specific sequences convey different information. Communication module 102 may also receive communication signals for potential action by processing module 110.

In some embodiments, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby potentially increasing the battery life of LCP 100. In other instances, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip.

Processing module 110, in additional embodiments, may include a memory circuit and processing module 110 may store information on and read information from the memory circuit. In other embodiments, LCP 100 may include a separate memory circuit (not shown) that is in communication with processing module 110, such that processing module 110 may read and write information to and from the separate memory circuit. The memory circuit, whether part of processing module 110 or separate from processing module 110, may be volatile memory, non-volatile memory, or a combination of volatile memory and non-volatile memory.

Collectively the processing module 110, mechanical sensing module 108, electrical sensing module 106, pulse generator module 104, and communication module 102 may be referred to as the operational circuitry of the LCP. In some examples the individual modules 102, 104, 106, 108, 110 may be subcomponents on a single hybrid or circuit board, or even within a single VSLI or ASIC, or may be spread across several hybrids, circuit boards, VSLI or ASIC components. In some examples, certain elements of processing module 110 are performed in the digital domain—such as determining whether to deliver therapy and operating the communication module when awoken for such a purpose—while others are performed in the analog domain—such as ongoing monitoring of the received electrical and/or motion signal until a significant perturbation of either signal or a timeout occurs, allowing the digital circuitry to stay in a low power state by duty cycling to sleep. On whole, the operational circuitry may be configured to perform the various methods shown herein and below claimed, by reference to memory and/or by operation of application-specific circuitry and/or ASIC chips.

Energy storage module 112 may provide a power source to LCP 100 for its operations. In some embodiments, energy storage module 112 may be a non-rechargeable lithium-based battery. In other embodiments, the non-rechargeable battery may be made from other suitable materials. In some embodiments, energy storage module 112 may include a rechargeable battery. For embodiments with a rechargeable battery, there may additionally be a recharging circuit using, for example, a coil that receives an electrical or magnetic field to facilitate recharging transcutaneously, as is well known in the art. In other embodiments, biological energy capture devices may be used to take advantage of energy that can be generated using the cardiac or other biological motion. In still other embodiments, energy storage module 112 may include other types of energy storage devices such as super capacitors.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. The one or more anchors 116 are shown schematically in FIG. 1. The one or more anchors 116 may include any number of fixation or anchoring mechanisms. For example, one or more anchors 116 may include one or more pins, staples, threads, screws, helix, tines, and/or the like. In some embodiments, although not shown, one or more anchors 116 may include threads on its external surface that may run along at least a partial length of an anchor member. The threads may provide friction between the cardiac tissue and the anchor to help fix the anchor member within the cardiac tissue. In some cases, the one or more anchors 116 may include an anchor member that has a cork-screw shape that can be screwed into the cardiac tissue. In other embodiments, anchor 116 may include other structures such as barbs, spikes, or the like to facilitate engagement with the surrounding cardiac tissue.

In some examples, LCP 100 may be configured to be implanted on a patient's heart or within a chamber of the patient's heart. For instance, LCP 100 may be implanted within any of a left atrium, right atrium, left ventricle, coronary sinus, or right ventricle of a patient's heart. By being implanted within a specific chamber, LCP 100 may be able to sense cardiac electrical signals originating or emanating from the specific chamber that other devices may not be able to sense with such resolution. Where LCP 100 is configured to be implanted on a patient's heart, LCP 100 may be configured to be implanted on or adjacent to one of the chambers of the heart, or on or adjacent to a path along which intrinsically generated cardiac electrical signals generally follow. In these examples, LCP 100 may also have an enhanced ability to sense localized intrinsic cardiac electrical signals and deliver localized electrical stimulation therapy.

In some instances, LCP 100 may be configured to deliver rate-adaptive pacing therapy to a patient's heart. For instance, LCP 100 may be configured to deliver electrical stimulation pulses to the heart of the patient on an on-going basis to help ensure that the patient's heart contracts in a safe and effective manner. LCP 100 may additionally sense one or more signals, for example using electrical sensing module 106 and/or mechanical sensing module 108, and determine, based on the sensed one or more signals, whether to change the rate of delivery of the electrical stimulation pulses.

For example, based on the sensed one or more signals, LCP 100 may determine that there is less of a need for cardiac output, and may decrease the rate of delivery of the electrical stimulation pulses. In other instances, based on the one or more sensed signals, LCP 100 may determine that there is a need for increased cardiac output, and may increase the rate of delivery of the electrical stimulation pulses. Adjusting the rate of delivery of the electrical stimulation pulses based on the sensed one or more signals may extend the battery life of LCP 100 by only requiring higher rates of delivery of electrical stimulation pulses when the sensed one or more signals indicate there is a need for increased cardiac output. Additionally, adjusting the rate of delivery of the electrical stimulation pulses may increase a comfort level of the patient by more closely matching the rate of delivery of electrical stimulation pulses with the cardiac output need of the patient.

Where LCP 100 adjusts the rate of delivery of electrical stimulation pulses based on the sensed one or more signals, LCP 100 may in some cases determine a respiration rate based on the sensed one or more signals. Respiration rate may be indicative of a relative cardiac output need for the patient. For example, an increased respiration rate may indicate that there is a need for increased cardiac output, and a decreased respiration rate may indicate less of a need for cardiac output. Accordingly, and when so provided, LCP 100 may adjust the rate of delivery of the electrical stimulation pulses based on the determined respiration rate.

In at least some examples, LCP 100 may include a motion sensor (such as an accelerometer) and may determine a measure related to the respiration rate based on the sensed motion sensor signal. Where LCP 100 is implanted on a patient's heart or within the heart, the motion sensor signal may include signals indicative of movement related to a number of different causes. For instance, the motion sensor signal may include movement related to the gross movement of the patient, such as walking, bending, or other gross body movements. Additionally, the motion sensor signal may include movement related to the contraction of the heart, particularly when LCP 100 is implanted on or within the heart. Additionally, the motion sensor signal may include movement related to the inhalation and exhalation of the patient (i.e. respiration). For instance, as a patient breathes in and out, the lungs apply different pressure to the heart and the intrathoracic pressure changes accordingly. This change in the intrathoracic pressure may cause changes in the shape and size of the various chambers of the heart, as well as the movement of the heart and the heart chambers. After inhalation, the intrathoracic pressure may be relatively higher, which may decrease the volume of blood that flows into one or more of the chambers of the heart during a cardiac cycle. Conversely, after exhalation, the intrathoracic pressure may be relatively lower, which may allow relatively more blood to enter the chambers of the heart during a cardiac cycle. These differences in the amount of blood flowing into and out of the heart and any movement of the heart or heart chambers due to the changes in intrathoracic pressure may be contained in the motion sensor signal.

A motion sensor may be used to measure inotropic changes in the myocardium; either positive or negative changes. Patients having chronotropic incompetence can still have appropriate contractility responses to increased metabolic demand. For example with increased metabolic demand, contractility increases due to adrenergic excitation. The opposite occurs with decreased metabolic demand.

Although an LCP serves as the platform for much of the below description and above detail, any implantable device having a motion sensor may take advantage of the presently described enhancements. Other devices may include drug or other substance delivery systems, neurostimulator or neuromodulation systems, and implantable cardiac monitoring systems, for example.

Figure 2:
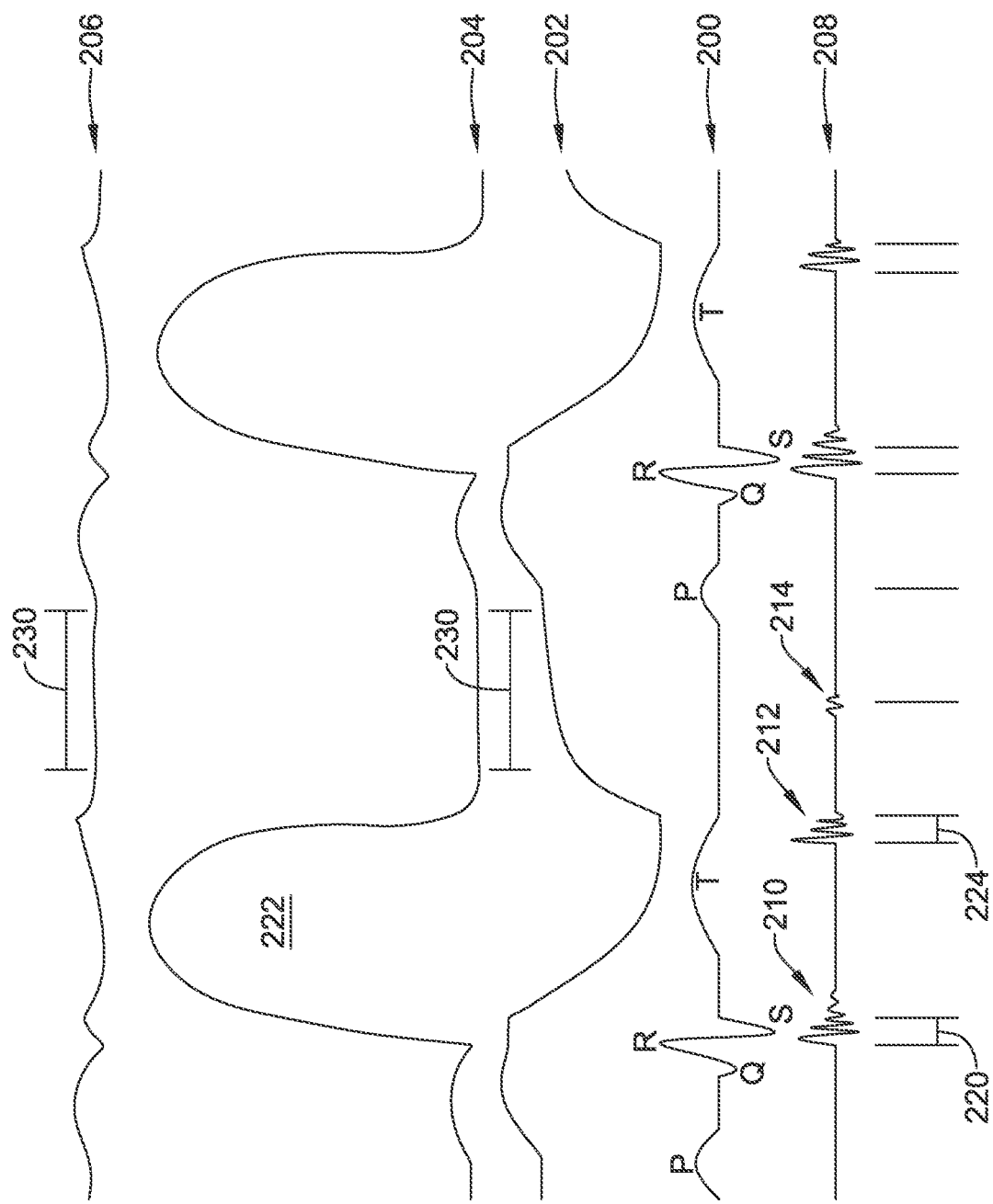
FIG. 2 is a graphic showing cardiac electrical events and intracardiac pressure and volume measurements on a single timeline.

FIG. 2 shows several different biological signals in a time-sequenced fashion. For example, the electrocardiograph is shown at 200, including well known P-Q-R-S-T wave sequences as the heart beats. These "waves" represent the electrical signals that flow through the myocardium to trigger muscle contractions during depolarization and subsequent repolarization. At 202, the ventricular volume is represented, with volume peaking at the time of the QRS complex and dropping in response to muscle contraction caused by the QRS complex, with refilling starting as after cardiac repolarization represented by the T-wave.

At 204, the ventricular pressure is represented, with a peak at 222 as the cardiac volume decreases (shown by line 202). Atrial pressure is represented at 206. The atrial pressure 206 illustrates changes that are much smaller than those of the ventricles.

The phonocardiogram is shown at 208, with the first heart sound at 210, over the QRS complex during systole, the second heart sound 212 representing the end of systole and start of diastole, and the third heart sound 214 occurring still later. The first heart sound 210 corresponds to closing of the atrioventricular valves, that is, the tricuspid and mitral valves. The second heart sounds 212 correspond to closure of the aortic and pulmonary valves. The third heart sound 214 is generally less common and of lower amplitude than the first two heart sounds 210, 212 and may relate, it is thought, to blood filling the ventricles. The motion and sounds represented by the changing ventricular volume 202 and heart sounds 210, 212, 214 can all create interference for a motion sensor, which may be sensitive to each of these.

The inventors have recognized that a useful goal in this context is to identify a relatively quiet period of time, illustrated at 230, during which cardiac-sourced interference is reduced. Although the third heart sound 214 may overlap this period 230, it should be noted that the third heart sound 214 is not universally observed and is the lowest amplitude of the heart sounds and so is less likely to cause significant interference. The inventors have recognized that an LCP may be configured for temporal avoidance of cardiac motion interference, enhancing the signal for analysis and potentially avoiding or reducing computational burden associated with other filtering techniques.

Figure 3:
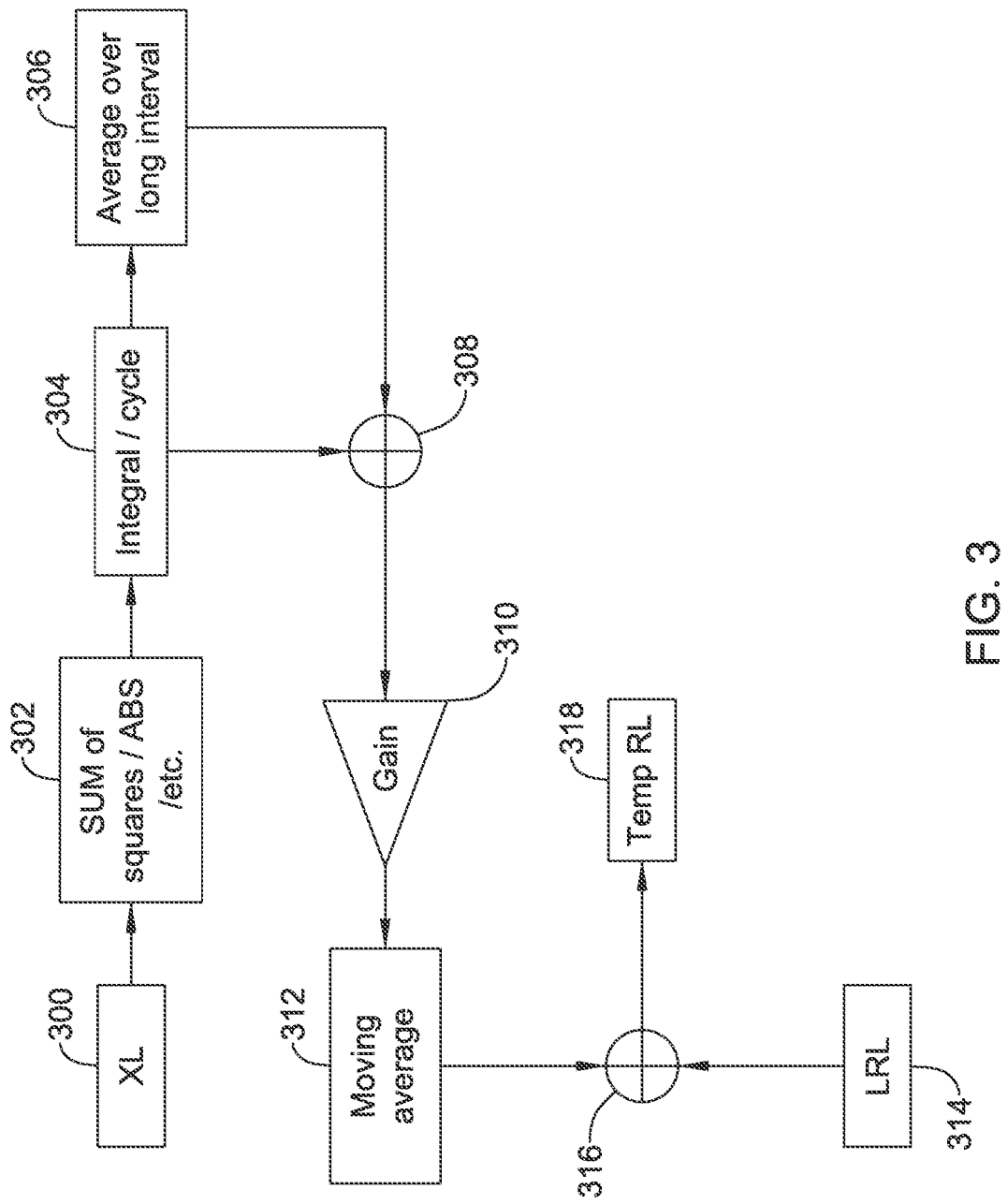
FIGS. 3-6 show several data flow arrangements for illustrative motion sensors.

FIGS. 3-6 shows several data flow arrangements for illustrative motion sensors. FIG. 3 shows a first example. A sample is taken at 300. The "sample" may represent several discrete data elements. For example, a sample may include data points captured for each of several axes of a multi-axis accelerometer (X, Y, Z, for example) that may serve as a motion sensor; such a sample may be thought of as a vector sample with elements $\{x[i], y[i], z[i]\}$. Moreover, a sample may include several close-in-time data points. For example, when "sampling" is performed on a single axis of the output of the accelerometer, 2 or more data points (for example, 2 to 20 data points) may be taken. In one example, four data points may be captured at 400 Hz, yielding a 10 millisecond slice of the output signal as the sample; other rates and quantities may be used. Thus a single sample from a three axis accelerometer could be thought of as a matrix such as:

$x[i], x[i+1], x[i+2], x[i+3]$
$y[i], y[i+1], y[i+2], y[i+3]$
$z[i], z[i+1], z[i+2], z[i+3]$

The math is not so simple as a single number coming out. Computational burdens are presented by such math in an implanted system.

Sampling may be called on a constant basis; historically accelerometer or motion sensor outputs in implantable medical systems would be sampled at rates of 10 to 50 hertz. However, in examples further shown below, sampling occurs in response to detected heart beats identified by analyzing the cardiac electrical signal. For example, the cardiac electrical signal (sometimes referred to as the cardiac electrogram, if captured from within the heart, or electrocardiogram, if captured outside the heart) may be compared to a time-varying threshold to identify the R-wave or QRS complex representative of an individual cardiac cycle. If desired, as alternatives, heart sounds or blood pressure measurements may instead be used to identify a cardiac cycle. As discussed further below, when taking one or more samples with each cardiac cycle, timing of the samples is be selected, in some examples, to avoid certain noise sources.

In the example of FIG. 3, a single axis or multiple axes may be under analysis, with individual samples having several close in time data points. Since there are several data points, the individual data points may be passed on, or may be processed at 302 to take a sum of squares, absolute value sum, mean, or max value, as desired. An integral is taken of the several data points in a given sampling cycle at 304. The integration at 304 may be omitted if a single data point is taken as the sample The output of the integral 304 is averaged over a long interval at 306 to yield a baseline. At 308, the instantaneous output from block 304 is compared by subtraction to the long interval average from block 306. The difference may be multiplied in a gain stage at 310 and fed into a moving average block 312, to allow smoothing of the motion sensor signal. For example, a patient rolling over in his or her sleep could be detected as significant motion by such a system, but the moving average block 312 would smooth this large motion over a period of in the range of 5 to 30 seconds. Such smoothing would avoid inappropriate rate response to isolated motion.

For simplicity, several examples herein refer a difference being calculated. In some examples, a difference is calculated relative to a baseline by subtraction. In other example, a difference may be a ratio of a measured value to a baseline value, that is, if the baseline is represented by a non-zero measurement output, the difference may be the ratio to the non-zero output. The word difference is intended to cover all such permutations of a comparison to baseline to determine a difference.

The moving average 312 may then be compared at 316 to a rate response level 314 representing the current state of rate response. For example, if the current state is at a base pacing level—that is, no rate response, then the level 314 may be zero, and an increase would be identified if the moving average is greater than level 314. The output 318, which is the temporary response level, is used to modify the existing state.

In some examples, the various blocks shown in FIG. 3 (and further below in FIGS. 4-11) may be implemented as instruction sets stored in non-transitory medium, such as the memory of an implantable medical device, for operation by a microprocessor or microcontroller. In other examples, a state machine architecture may be used with various operations taking place under control of the device as it progresses through a series of analytical states. In some examples, one or more blocks in FIGS. 3-11 may be performed by application specific integrated circuit hardware or other dedicated hardware. For example, processing and integration blocks 304, 306 may be performed by dedicated hardware, while other blocks are performed within a microprocessor.

Figure 4:
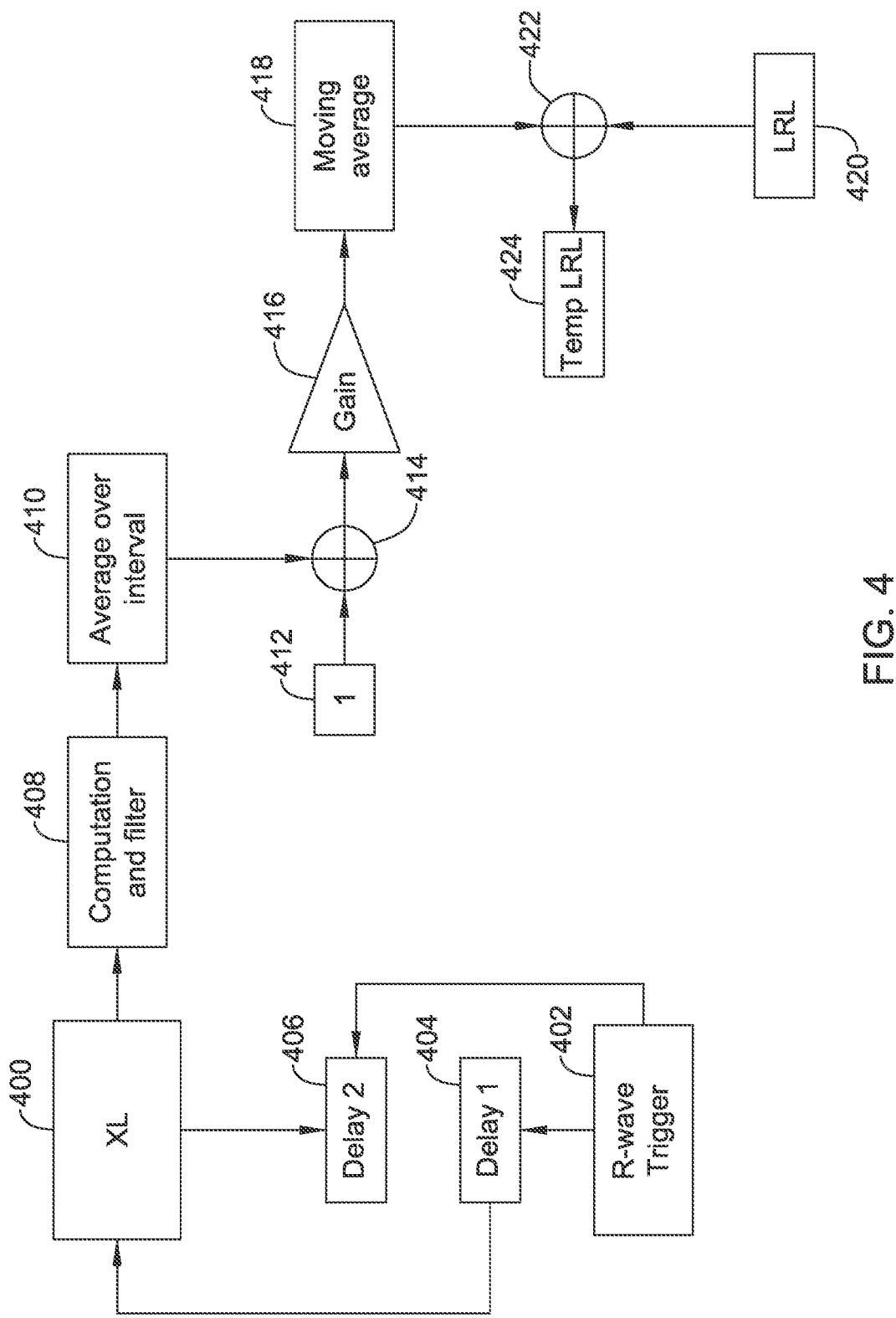

FIG. 4 shows another example. Here, sampling is performed at block 400 on the basis of a trigger such as an R-wave trigger 402. The R-wave trigger 402 may be more broadly thought of as a trigger based on a predefined electrical cardiac event occurring. For example, a cardiac electrical signal may be monitored using electrodes (such as electrodes 114, 114' of FIG. 1) and compared to a threshold; when the threshold is crossed, a predefined electrical cardiac event is found to have occurred. The threshold may be time-varying and may be adaptive to the sensed cardiac electrical signal amplitude using various known methods in the art. Sampling may occur at first and/or second delays 404, 406 after the trigger event 402 is identified. While several of the below examples focus on identifying a useful delay, it is noted that more than one delay may be selected to take two samples from within one cardiac cycle.

The output sample is may go through computation and filtering 408 (such as amplifying, root-mean-square assessment, smoothing, etc.) and an average signal within the sample may then be calculated at 410. The pre-processing at blocks 408, 410 may be on a per-sample basis, or may be performed for all samples (if multiple are taken) within a cardiac cycle, if desired. The pre-processed sample can be compared to a long term average 412 in block 414, processed further with an optional gain stage 416, and smoothed to generate a moving average at 418. As with FIG. 3, the moving average 418 can then be compared at 422 to the existing activity calculation 420 to yield a change, if needed, to the activity calculation at 424.

In a further example, the trigger 402 may be either a detected cardiac event, if one occurs, or pace delivery if the bradycardia pacing escape threshold is exceeded. In such a design, the first delay 402 may be configured for intrinsic (non-paced) cardiac cycles, and the second delay 404 may be configured for paced cardiac cycles. This accounts for the differences between intrinsic and paced cardiac cycles since, for example, the paced cycles may have different conduction characteristics and wider QRS complexes than intrinsic beats.

Figure 5:
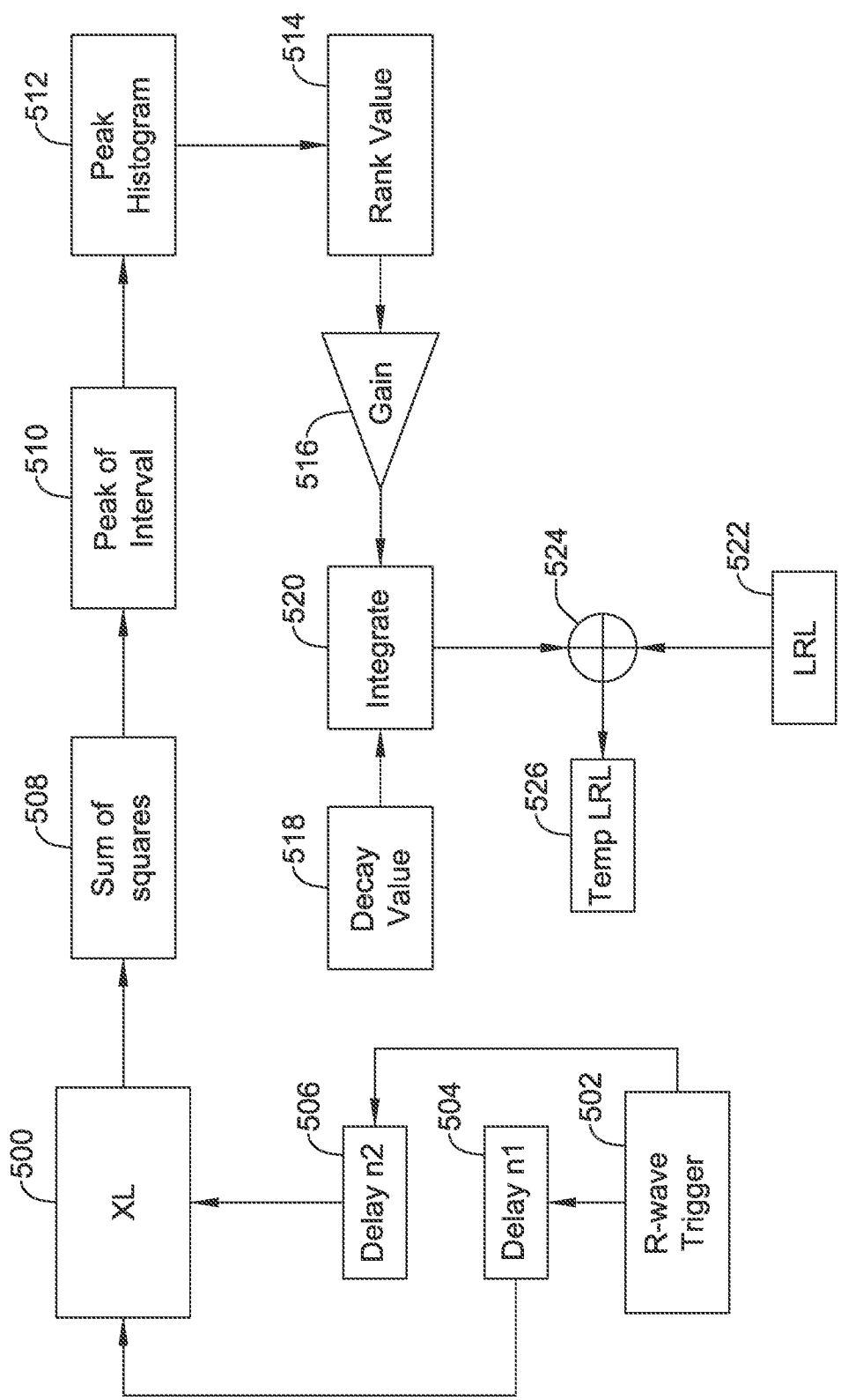

FIG. 5 shows another illustrative example. Here, the sample again is taken at 500, based on a trigger 502 and one or more delays 504, 506. In some examples, the delay(s) are selected to identify a "quiet" phase of the cardiac cycle where the heart is not moving significantly. In other examples, the peak activity phase of the heart may be sought to assist in characterizing the physiology thereof for example by identifying certain heart sounds and specifying cardiac motion.

Again, the sample 500 is pre-processed at 508 using, for example, a sum of square approach or the like, and one or more peak motion detection from the interval are identified at 510. For example, it may be desirable to take a comprehensive view of the cardiac motion artifact by sampling at a number of times within a cardiac cycle to then identify peaks and generate a histogram 512. Rank valuation can then be performed at 514, and one or more peaks passed through to the gain and integration stages 516, 520. A decay value may be incorporated as well from block 518 with the decay representing expected value within a cycle. These outputs may be used to compare to the existing state 522 in a comparison at 524 to yield an adjustment calculation 526. In other examples the method may stop with the histogram at 512 which may be useful to monitor, for example, the stages (strength or duration, for example) of cardiac contraction.

Figure 6:
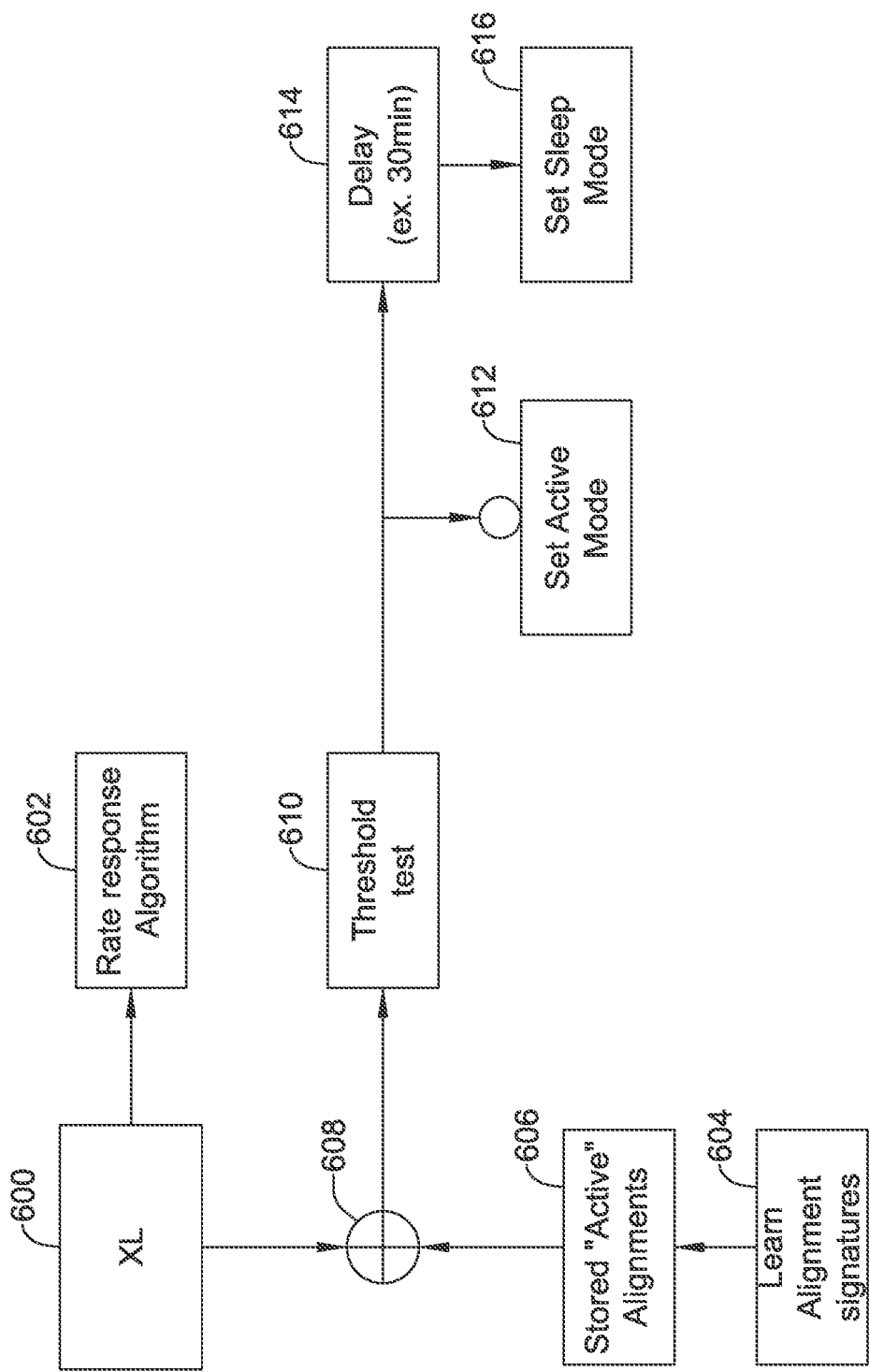
Figure 7:
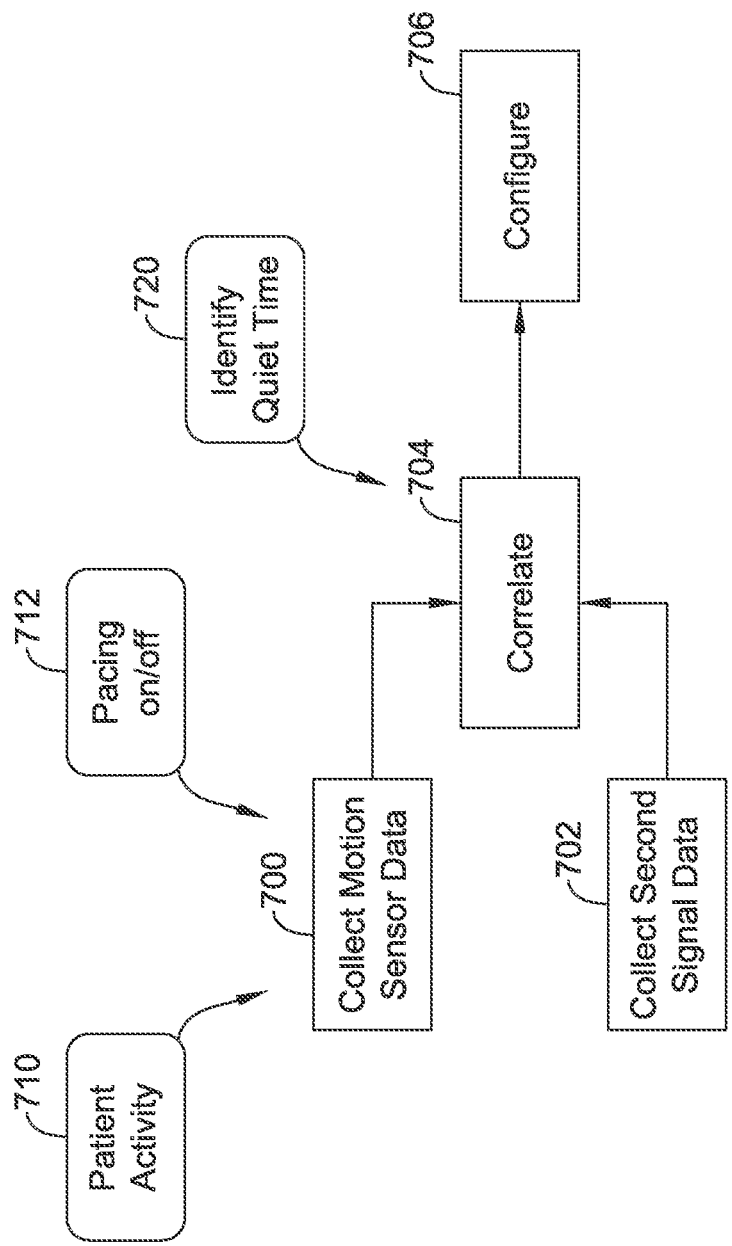
FIGS. 7-11 show several illustrative process flow diagrams.

FIG. 6 shows another illustrative example. In this example, when a sample is taken at 600 from the motion sensor, the sample can be passed forward to one of the above or below described methods of analyzing the motion sensor output. In addition, the output can be provided to a comparison module at 608. In this "learning" example, a device is provided the opportunity to observe, at relatively high sampling rates (10 to 100 Hz for example) motion sensor output across the entire cardiac cycle for a short period of time—perhaps a few seconds up to a few minutes while a patient is active and/or at rest. Observing such an overall cycle while in multiple states can facilitate the development of an alignment signature 604 indicative of whether the patient is in a specific state. One state of particular interest to reduce energy consumption is the state of rest or sleep.

Alignments for one or more states, including an active state, or, alternatively, a sleep state, can be stored at 606 for use in the comparison at 608. A match threshold is applied at 610 to determine whether there is a match to an active or sleep state. If an active state is identified or cannot be eliminated, then the active motion sensor tracking mode may be set at 612. Otherwise, a passive motion sensor tracking mode is set and kept in place for a delay period, as indicated at 614, and the motion sensor subcomponents of the implantable medical device are put to sleep at 616 until the delay period expires. Illustrative delay periods may range from a minute to an hour. In one example, if the patient appears to be asleep or inactive, a thirty-minute delay is set to conserve energy.

A sleep function as shown in FIG. 6 may be called when the patient's activity level according to the rate response algorithm 602 is at baseline or minimum. In another illustration, a method or device may require the patient's activity level be at baseline for a specified period of time before attempting to determine if the patient is asleep. In another illustration, the delay period may be initially short in a first iteration (for example, 5 minutes) and then extended if the patient appears to remain asleep to longer intervals until a maximum sleep interval is reached. In yet another illustration, if the patient's sensed cardiac rate rises above a preset threshold for a predetermined period, sleep mode 616 may be interrupted.

FIGS. 7-11 show several illustrative process flow diagrams. Starting at block 700, motion sensor data is collected, as well as a second signal data 702, preferably contemporaneously though not necessarily concomitantly. For example, motion sensor data may be captured at a first interval using a first sampling period/repeat rate, while the second sensor data may be captured according to a second timing scheme. In an illustration, motion sensor data 700 may be captured in sets of data points, with each set being a sample, captured at a rate of 50 Hz to 1000 Hz, with sets of 1 to 20 data points, captured in groups at rates of 10 Hz to 50 Hz, while the second sensor data 702 is captured continuously at a rate of 100 to 1000 Hz, with 256 Hz being illustrative. In one embodiment the second signal data is the cardiac electrogram. In another embodiment the second signal data is blood pressure data, which may be captured at a lower rate, but more continuously, than the motion sensor data.

The motion sensor data and second signal data are aligned and correlated at 704, and used to generate a configuration for the motion sensor data 706. For example, the aligning and correlating step may be performed to facilitate identifying a quiet time 720 in the motion sensor data relative to alignment or reference points in the second signal data 702.

To further facilitate the configuration, patient activity 710 and/or the status of pacing therapy 712 can be controlled. For example, the data collection 700, 702 is performed, in one illustration, while the patient is told to remain at rest, thus controlling patient activity 710. In this state, the motion sensor should only identify motion caused by cardiac motion and/or sounds within the heart—since an accelerometer-based motion sensor may be sensitive to vibrations ("sounds") occurring in the heart. Thus a quiet phase of the motion sensor output would provide a good baseline for identifying patient activity. The process may be repeated with pacing on and off, as indicated at 712, to ensure that quiet times 720 can be identified in either circumstance. Moreover, if the quiet time shifts based on whether pacing is on or off, the configuration 706 would be adjusted to ensure the right quiet time is selected for both paced and non-paced beats.

It is envisioned that a system will operate in a learning mode—that is, the system may not necessarily rely on specific landmarks or theoretical bases when selecting a quiet time. However, in reality, it is expected that devices will choose a time period as indicated by FIG. 2 above at 230, a period between the T-wave and the P-wave when the cardiac signal is in a quiescent phase. The configuration 706 that will then be stored would take the form of a value or values indicating an appropriate delay from the QRS complex or R-wave to the expected quiet time.

Alternatively, sampling, with or without delays may be triggered by a different detectable event. For example, the configuration 706 may store a time period from the T-wave or end of the T-wave. The configuration 706 may instead be reflected in identification of a quiescent state of the electrocardiogram where the ECG or EGM is electrically at baseline for a period of time, as such a state would correspond to the period between the T-wave and the P-wave.

For those patients who exhibit a detectable third heart sound, the configuration 706 may be selected to ensure motion sensor sampling before or after the third heart sound in order to avoid it. Such a result may occur from the device learning when a quiet time takes place relative to one or more cardiac signals, or it may be ensured using inputs from a physician.

In some examples a further set of manipulations of the state of the patient may be had. Configuration may be performed while the patient is in a state of rest as well as during patient activity selected to increase the heart rate. In conjunction with the patient activity the output pacing rate may be increased by the implantable device, if needed. For example, a baseline configuration may be used during a learning period and, once data capturing and correlation steps are completed, a tailored configuration can be stored for the patient. By rechecking the configuration at increased heart rates, the appropriate timing of the quiet time at various heart rates can be determined and stored as part of the configuration 706.

In one example, the pacing rate may be increased to confirm the mechanical quiet phase remains quiet at increased rates (or, if the timing of the quiet phase moves, to allow for adjustment). That is, if the quiet time at low rates is no longer quiet at high rates due to motion intrinsic to the heart, the configuration of the quiet time can be adjusted. The quiet time may be preferably selected to avoid inappropriate feedback from the heart itself, which could perpetuate an unnecessarily high cardiac rate if not avoided.

Much of the above presumes a ventricular placement of the implantable device. If an implantable device is placed in the atrium, it may be more suitable to use the P-wave as a trigger point, since it will be the larger signal to the atrial device absent cross-chamber noise. In this instance, the implantable device is more likely to identify a quiet time that may occur during systole, that is, while the ventricles are ejecting blood to the rest of the body.

Figure 8:
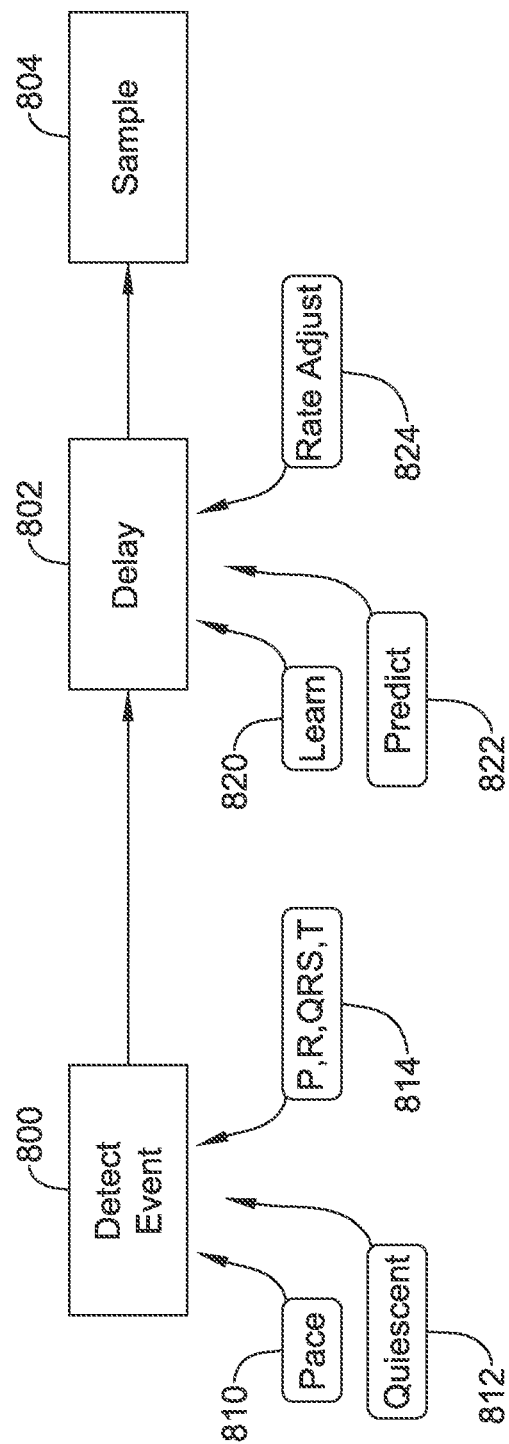

FIG. 8 shows another example. In this example, the system is shown in more of an operational state. An event is detected at 800. The device will perform sampling of a motion sensor output at 804 in response to the detected event from 800. In some examples, a delay period 802 first must expire prior to the sampling at 804.

Within FIG. 8, the detected event, in some examples, may be the delivery of a pacing output 810, either by the implantable device or by a second implantable device. In another example, the detected event may be the detection of a quiescent state 812 where, for example, the cardiac electrogram remains stable for a period of time (such as 40 milliseconds, about 10 samples at 256 Hz). In another example, the detected event is a predefined event in the electrical cardiac signal such as a P-wave, R-wave, QRS complex or T-wave, as indicated at 814.

The delay 802 may be defined or determined in a number of ways. In some examples, a learning process is used at 820, such as the process of FIG. 7 where the motion sensor output and a second signal are analyzed to look for quiet times in the motion sensor output while the patient is in a controlled state. In another example noted at 822, the delay can be based on a predictive formula; for example, using Bazett's formula or Friderica's formula, the R-T interval can be predicted from a known cardiac beat rate, and the delay can be set to cause sampling after the T-wave is completed. In a still further example, the delay 802 may be adjusted in light of the cardiac rate of the patient, as shown at 824. For example, at higher rates a shorter delay may be needed. Such adjustments in 824 may be made based on learning 820 or prediction 822.

Figure 9:
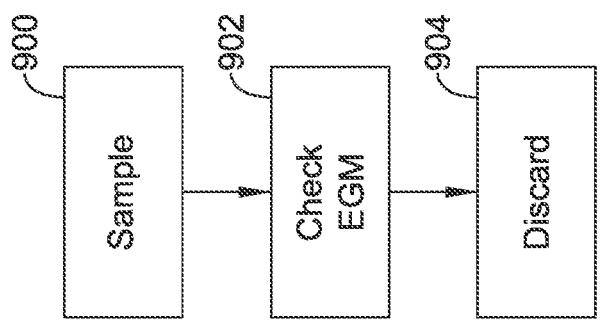

FIG. 9 illustrates a data correction method that may also be used. Following capture of a sample at 900, a device checks a second signal, such as the electrogram, as noted at 902. If a particular event is identified in the second signal, the sample can be discarded, as noted at 904. For example, supposing sampling takes place in response to the R-wave and is intended to occur after the T-wave and before the P-wave, if the check of the second signal electrogram at 902 shows that the T-wave overlaps or P-wave precedes the sample 900, then the quiet phase of the cardiac motion may have been missed. This suggests a sample which may be noisy and may mix or overlap patient motion and cardiac motion. Thus the sample is discarded at 904. Repeated discarding may result in a decision to reconfigure the sampling system, implementation of a higher power approach to sampling (higher duty cycle), or activation of a patient or physician alert function.

Further to the example of FIG. 9, rather than a P-wave or T-wave overlap, the presence of another signal in the electrogram at 902 can trigger discarding the sample. For example, a conducted atrial arrhythmia, or a ventricular extra-systolic beat (such as a premature ventricular contraction) identified within the cardiac electrical signal, or by some other sensor such as heart sounds or a pressure sensor, for example, may be identified at block 902 and used as a basis for discarding a motion sensor signal. The circuitry feature, or software function, which performs such identification may be spurious event identifier.

Figure 10:
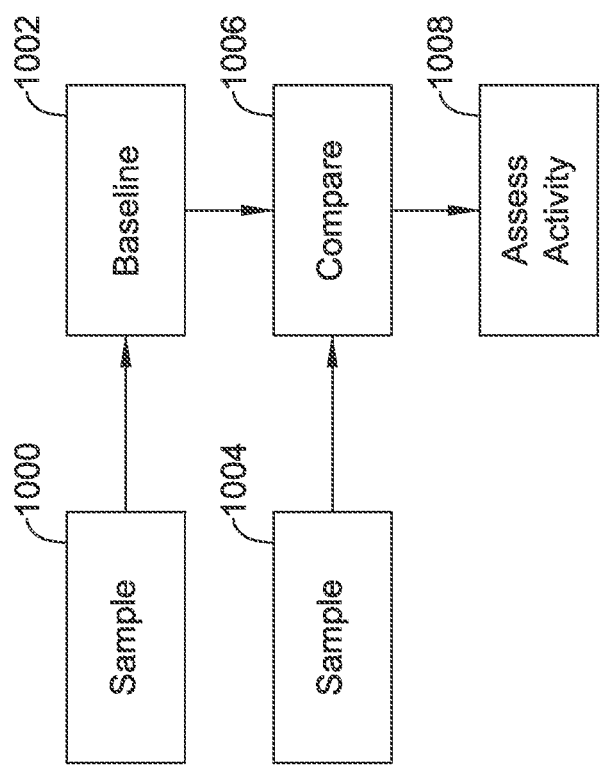

FIG. 10 shows another illustrative example. Here, motion sensor samples are captured at 1000. A large number of such samples are averaged over time to generate a baseline motion for the patient. If desired, statistical methods may be used to eliminate outlier data prior to setting the baseline by, for example, eliminating samples more than two standard deviations away from a mean. The baselining step 1002 may occur while a patient is ambulatory but more preferably would take place in a controlled setting with the patient generally at rest.

Once a baseline is established at 1002, a sample is taken at 1004. The sample 1004 is then compared to the baseline at 1006, to generate a difference that is used to assess patient activity at 1008. If desired, several samples may be taken and averaged together, or a smoothing function may be applied to a series of samples prior to comparing to the baseline 1006.

Figure 11:
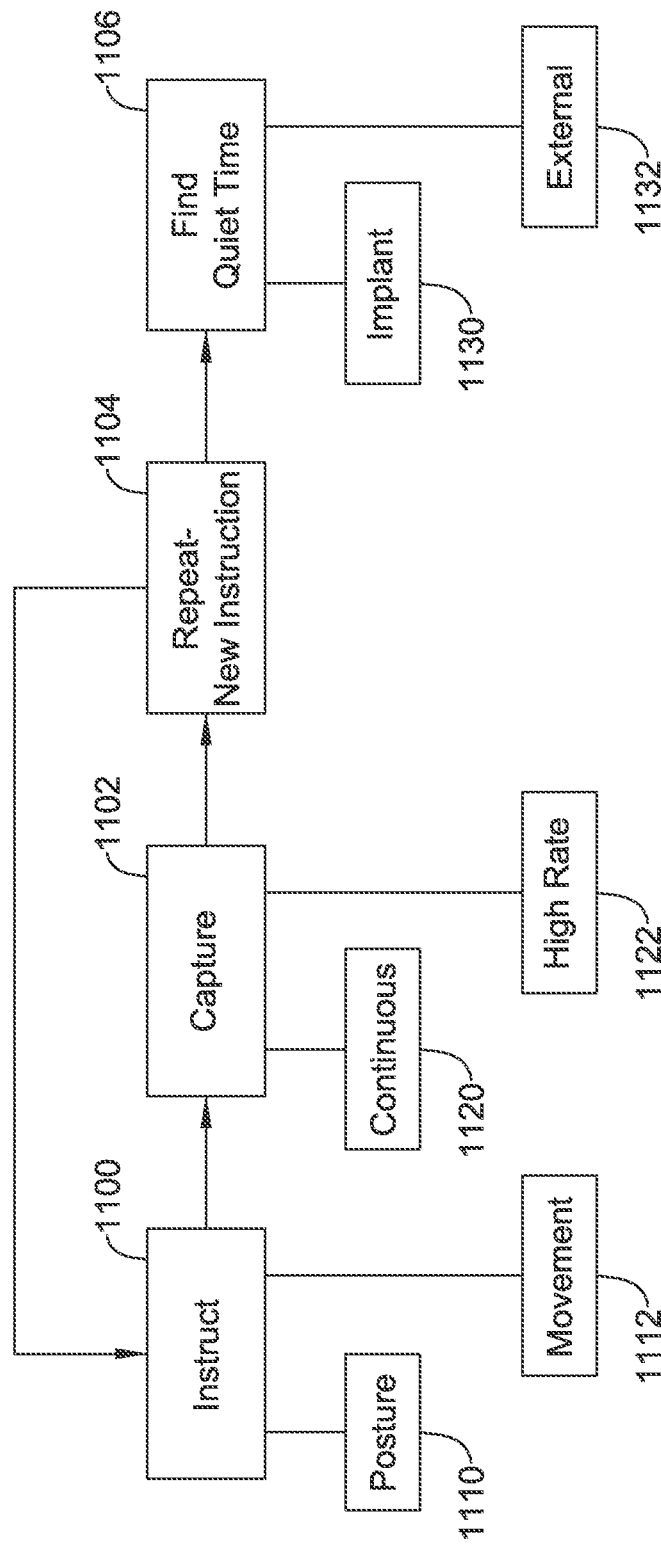

FIG. 11 shows a clinical method of establishing a patient configuration. Here, the patient is instructed at 1100 to assume a posture, for example as shown at 1110. Sitting, supine, prone, laying on left or right sign, standing, or other postures may be chosen at 1110. Alternative, the patient is instructed 1100 to engage in a movement, such as walking, jogging, or a favorite exercise, or to hold still or engage in the Valsalva maneuver, as indicated at 1112.

Next, data capture is performed at 1102. Data capture may include capturing data from a motion sensor as well as a second data input or sensor such as the electrogram. Capture of the motion sensor output and second signal may be continuous 1120 or at high rate 1122 for the purposes of configuration, with the intent being that once configuration is completed a lower rate may be implemented.

Steps 1100 and 1102 may be repeated as shown at 1104 with new instructions to the patient for second and subsequent iterations. Once data is captured, the method determines a quiet time in the motion sensor signal using a trigger or reference point identified in the second signal data. The analysis of this type may be performed by the implanted device 1130 or may be performed by an external device in communication with an implanted device 1132.

Figure 12:
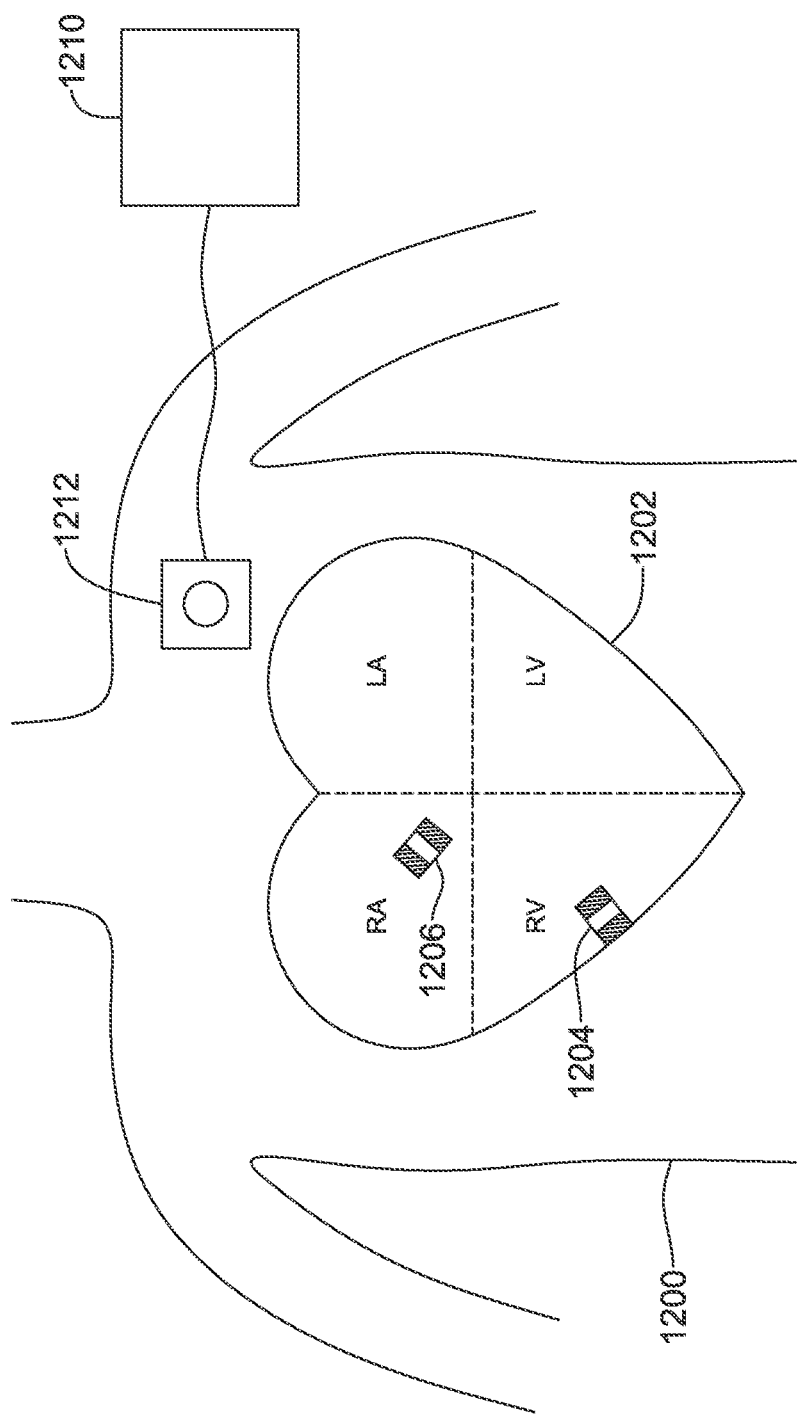
FIG. 12 shows a patient having an implantable medical device system in the heart.

FIG. 12 shows a patient having an implantable medical device system in the heart. The patient 1200 is shown having a heart 1201 in which a plurality of medical devices are implanted. In this example, a ventricular device is shown at 1204 and an atrial device at 1206. The implantable devices 1204, 1206 may operate independent of one another or may coordinate using conducted communication—or other communication such as RF—therebetween. An external device 1210 such as a programmer is also shown, in this instance with a wand 1212 for placement on the patient to facilitate communication to the implantable devices 1204, 1206.

It is not necessary to have multiple implanted devices, but it is envisioned that at least some patients will have multiple devices. In some examples, one or both implanted device 1204, 1206 has a motion sensor. In some examples, the motion sensor of one of the devices is disabled after configuration has been performed, if it can be determined that performance of one or the other is better or worse and the devices operate in coordination with one another. In some examples, an atrial device 1206 may be of smaller size and lesser mass, and omits a motion sensor which is instead provided in the ventricular device 1204.

Alternatively, the devices may be identical and whichever device has a greater available battery capacity is used for motion capture, while the other device renders a motion sensor inactive. For example, it may be that the atrial device 1206 is anticipated to use less power in therapy delivery than the ventricular device 1204, such that motion sensing is performed with just the atrial device 1206.

In some examples, the two separate devices 1204 and 1206 may provide synchronized motion capture to identify an appropriate configuration. For example, both devices 1204 and 1206 may communicate captured motion data out to the external programmer 1210, where the motion sensing data is captured in overlapping time periods. Motion that is sensed due to patient movement should be identified in both of the devices, while local motion from cardiac chamber movement, for example, would not necessarily show up in each device's motion sensor output. By comparing the signals, the bodily motion signal can be extracted. Next, working backwards, it would be determined which time periods in one or both implanted devise 1204 and 1206 is capturing the bodily motion accurately and without interference from local cardiac motion. A configuration would be identified and stored for one or both implanted devices 1204 and 1206.

A first non-limiting example is an implantable device (ID) comprising a power source, operational circuitry, a motion sensor, and electrodes, the electrodes configured to capture a cardiac electrical signal, wherein the operational circuitry comprises: trigger means for determining that a predefined event has occurred in the heart of the patient using a signal from the electrodes; sampling means for sampling an output of the motion sensor in response to the trigger means. Illustrative examples of a trigger means includes a circuit (such as a comparator) or software implemented instruction for comparing a representation (analog or digital) of a received cardiac signal to a predetermined threshold such as a threshold as described in U.S. Pat. No. 8,565,878, the disclosure of which is incorporated herein by reference. Such triggers are also described above. Illustrative examples of sampling means include any suitable sampling circuit such as a capacitive sample and hold circuit in which, for example, an output is switched to a capacitor, charging the capacitor up or down to a level related to the sampled signal, and a comparator is used to drive a second capacitor to match the sampling capacitor, or a comparator circuit, and an analog-to-digital convertor capable of retaining or passing to memory an output of a measurement, among others. The drawings indicate certain examples including trigger 402 and sampling 400 in FIG. 4, trigger 502 and sampling 500 in FIG. 5, for example.

A second non-limiting example is the ID of the first non-limiting example, wherein the sampling means further comprises delay means for waiting a delay period following activation of the trigger means before sampling the output of the motion sensor. Illustrative delay means may include a timer and associated memory or comparator for setting the duration to run the timer, or may include a capacitor that can be charged to a selected level and then discharged in predictable fashion. Delay is illustrated in the Figures, for example, at FIG. 6, block 614, and FIG. 8, at 802.

A third non-limiting example is an ID as in the second non-limiting example, wherein the motion sensor is configured to operate in a low-power mode except to facilitate the sampling means taking a sample of the output thereof. A fourth non-limiting example is an ID as in either of the second or third non-limiting examples, wherein the predefined event is one of an R-wave, a pacing impulse, or a QRS complex, and the delay period is selected to expire prior to occurrence of a P-wave. A fifth non-limiting example is an ID as in any of the second to fourth non-limiting examples further comprising a spurious event detector configured to determine whether an event occurs during or after the delay period and, if so, the spurious event detector is configured to interrupt the sampling means or cause the sampling means to discard the sampled output of the motion sensor. A sixth non-limiting example is an ID as in the fifth non-limiting example, wherein the specified cardiac event is a ventricular contraction.

A seventh non-limiting example is an ID as in any of the second to sixth non-limiting examples, wherein the operational circuitry includes means for initializing the ID including: collection means to collect a set of data points from the motion sensor and from a cardiac electrical signal from the electrodes contemporaneously; correlating means to correlate time periods within the set of data points from the motion sensor to cardiac activity reflected by the cardiac electrical signal; and setting means to store information indicating when data from the motion sensor is to be captured by reference to specific repeatable elements of the cardiac electrical signal. Illustrative collection means may take the form of a memory location for receiving data for at least temporary storage. The correlating means may take any suitable form for comparing two shapes such as a correlation waveform analysis block or signal processing chip, or a microprocessor or microcontroller with associated memory instructions for comparing two shapes by difference of area, principal components, or wavelet analysis, for example. The setting means may include a volatile or non-volatile memory. An example is in FIG. 6, with collection at blocks 700 and 702, correlation at 704, and setting performed as the configuring step at 706.

An eighth non-limiting example is an ID as in the seventh non-limiting example, wherein the delay means is configured to calculate the delay period from the information stored by the setting means, taking into account a cardiac rate of the patient. A ninth non-limiting example is an ID as in any of the seventh or eight non-limiting examples, wherein: the correlating means is configured to determine when intrinsic mechanical motion of the heart is detected by the motion sensor relative to electrical signals of the heart; and the setting means is configured to store information indicating a time period relative to a specified electrical signal of the heart to avoid capturing intrinsic mechanical motion of the heart with the motion sensor. A tenth non-limiting example is an ID as in any of the seventh to ninth non-limiting examples, wherein the setting means is configured to set a delay to be triggered by detection of a T-wave in the cardiac electrical signal.

An eleventh non-limiting example is an ID as in any of the first to tenth non-limiting examples, wherein the ID includes pacing means to deliver pacing therapy to the patient and the predefined event is delivery of a pacing stimulus by the ID. Illustrative pacing means may include one or more of a voltage supply (such as an amplifier output), a current source (such as a current mirror), or a capacitor (or plurality thereof) or simply a battery output, coupled via the pulse generator module 104 (such as by a multiplexor, switch array or H-Bridge) to one or more of the electrodes 114, 114', for example, and associated instruction sets for operation by the processing module 110.

A twelfth non-limiting example is an implantable device (ID) comprising a power source, operational circuitry, a motion sensor, and electrodes, the electrodes configured to capture a cardiac electrical signal, wherein the operational circuitry comprises: sampling means for sampling a signal from a motion sensor in the ID; baseline calculation means for analyzing the sampled signal over time to generate a baseline output of the motion sensor; present state means for determining a present state indicator from the sampled signal; comparing means to compare the present state indicator to the baseline to yield a difference; activity characterizing means to analyze the difference to determine the patient's activity level. Illustrative sampling means may be as described above. Illustrative baseline calculation means may include analog or digital domain memory or storage locations for capturing an average sampled output of the motion sensor over time, with associated instruction sets for the processing module 110 to use for controlling baseline. For example, block 306 (FIG. 3) takes an average over a long interval to obtain a baseline; block 1002 (FIG. 10) likewise identifies a baseline using captured samples 1000.

Illustrative comparing means may include digital domain software instruction set or module for comparing two digital values, for example, or a comparator, for example, in the analog domain. A difference, as yielded, may be a subtractive difference, a ratio of two numbers/values, or other comparative output. Comparisons of this sort are noted at block 316 (FIG. 3), block 422 (FIG. 4), block 524 (FIG. 5), and block 1006 (FIG. 10).

The activity characterizing means may include a state machine, for example, which operates to change state based on the difference as calculated by the comparing means, for example, assuming baseline to a rest state for the patient, then a difference such as large subtractive difference, or large ratio to the baseline would suggest a high level of activity and be classified in an active state if meeting an active state threshold; and if the difference is a small subtractive difference or ratio, below an inactive state threshold, then the state machine may assume an inactive state. Other such means may be provided, using for example a stored memory location as a characterization of patient activity with plural possible values such as active, inactive, or hysteresis (in-between). Illustratively, the Temporary Response Level (Temp RL, at FIG. 3, block 318; FIG. 4, block 424, and FIG. 5 block 526) may be used as shown in the high level diagram of FIG. 10 to assess activity at block 1008 by the use of binning of the Temp RL to high or low classes, with or without a hysteresis band/bin in the middle. As noted, these may drive state machine logic in some examples.

A thirteenth non-limiting example is an ID as in the twelfth non-limiting example, wherein the baseline calculation means uses a number, M, of individual samples from the motion sensor; the present state means uses a number, N, of individual samples from the motion sensor; and M is an order of magnitude larger than N.

A fourteenth non-limiting example is an ID as in any of the first to tenth, twelfth or thirteen non-limiting examples, wherein the operational circuitry comprises: pacing means to deliver pacing therapy to a patient at a pacing output rate; activity determining means configured to use an output of the motion sensor to calculate an activity level of the patient; and adjusting means to adjust the pacing output rate in view of the activity level. Such activity determining means may be as noted in block 1008 of FIG. 10 and described above. The adjusting means may operate by increasing the pacing rate output when a higher level of patient activity is observed or likely, and reducing the pacing rate output when a lower level of patient activity is observed or likely, both within reasonable boundaries. That is such adjusting would have minimum boundaries (40 to 60 bpm, for example) and upper boundaries (120 to 200 bpm, for example) which may vary depending on patient characteristics and physician decisions.

A fifteenth non-limiting example is an ID as in any of the first to fourteenth non-limiting examples, wherein the ID is configured as a leadless cardiac pacing device for implantation entirely within the heart of the patient without a lead.

A sixteenth non-limiting example is a method of operation in an implantable device comprising: initializing an implantable device (ID) for disposition within the heart of a patient, the ID comprising a motion sensor for detecting movement of the patient, the initializing step being performed by: contemporaneously collecting a set of data points from the motion sensor and from a cardiac electrical signal; correlating time periods within the set of data points from the motion sensor to cardiac activity reflected by the cardiac electrical signal; and configuring the ID to capture data from the motion sensor by reference to specific repeatable elements of the cardiac electrical signal; using the ID as configured in the initializing step to capture cardiac signals of the patient and motion signals for the patient. A seventeenth non-limiting example is a method as in the sixteenth non-limiting example, further comprising; using the motion signals to determine an activity level of the patient; and setting and implementing a pacing rate for the patient using the determined activity level.

An eighteenth non-limiting example is a method as in either of the sixteenth or seventeenth non-limiting examples, wherein the step of configuring the ID to capture data from the motion sensor is performed by: determining when intrinsic mechanical motion of the heart is detected by the motion sensor relative to electrical signals of the heart; and setting a data capture period for the motion sensor relative to a specified electrical signal of the heart to avoid capturing the intrinsic mechanical motion of the heart with the motion sensor.

A nineteenth non-limiting example is a method as in any of the sixteenth to eighteenth non-limiting examples, wherein the step of configuring the ID to capture data from the motion sensor includes determining a delay after a T-wave in the cardiac electrical signal. A twentieth non-limiting example is a method as in the nineteenth non-limiting example, wherein the delay is configured as a function of cardiac rate. A twenty-first non-limiting example is a method as in the twentieth non-limiting example, wherein the cardiac rate is determined as a rate of pacing output of the ID. A twenty-second non-limiting example is a method as in the twentieth non-limiting example, wherein the cardiac rate is determined as an intrinsic rate of the patient's heart.

A twenty-third non-limiting example is a method of operating a motion sensor in an implantable device (ID) for disposition within the heart of a patient, the ID comprising a motion sensor for detecting movement of the patient, the method comprising: the ID determining a predefined event has occurred in the heart of the patient; and the ID waiting a predetermined period of time after the predefined electrical event and sampling an output of the motion sensor.

A twenty-fourth non-limiting example is a method as in the twenty-third non-limiting example, further comprising duty cycling the motion sensor to operate in a window corresponding to the sampling step and otherwise be in a low-power state. A twenty-fifth non-limiting example is a method as in either of the twenty-third or twenty-fourth non-limiting examples, wherein the predefined event is one of an R-wave, a pacing pulse, or a QRS complex, and the predetermined time period is selected to expire prior to occurrence of a P-wave. A twenty-sixth non-limiting example is a method as in any of the twenty-third to twenty-fifth non-limiting examples, further comprising using the output of the motion sensor to determine whether the patient is physically active to facilitate a rate-responsive pacing by the ID. A twenty-seventh non-limiting example is a method as in any of the twenty-third to twenty-sixth non-limiting examples, further comprising using the output of the motion sensor to determine an increase or decrease in cardiac contractility to facilitate a rate-responsive pacing by the ID.

A twenty-eighth non-limiting example is a method as in any of the twenty-third to twenty-seventh non-limiting examples, further comprising determining the predetermined period of time by using an accepted formula for predicting occurrence of a cardiac mechanical or electrical event. A twenty-ninth non-limiting example is a method as in any of the twenty-third to twenty-seventh non-limiting examples further comprising determining the predetermined period of time by initializing the ID by capturing a plurality of outputs from the motion sensor over a period of time including several heart beats to determine a mechanically quiet period in the patient's cardiac cycle relative to the predefined event.

A thirtieth non-limiting example is a method as in any of the twenty-third to twenty-ninth non-limiting examples, wherein the predefined event is one of a P-wave, an R-wave, a QRS complex, a T-wave, or a quiescent period. A thirty-first non-limiting example is a method as in any of the twenty-third to twenty-ninth non-limiting examples wherein the predefined event is delivery of a pacing stimulus. A thirty-second non-limiting example is a method as in any of the twenty-third to thirty-first non-limiting examples, further comprising analyzing a cardiac electrical signal of the patient during at least the predetermined period of time to observe whether a specified cardiac electrical event occurs and, if so, discarding the sampled output of the motion sensor. A thirty-third non-limiting example is a method as in the thirty-second non-limiting example, wherein the specified cardiac event is a ventricular contraction. A thirty-fourth non-limiting example is a method as in the thirty-second non-limiting example, wherein occurrence of the ventricular contraction is determined by identifying a P-wave, R-wave or QRS complex in the electrical cardiac signal at the same time as, or just before, the output of the motion sensor is sampled.

A thirty-fifth non-limiting example is a method of determining whether a patient is active using an implantable device (ID) for disposition within the heart of a patient, the ID comprising a motion sensor for detecting movement of the patient, the method comprising: sampling a signal from a motion sensor in the ID; analyzing the sampled signal over time to generate a baseline; generating a present state indicator from the sampled signal; comparing the present state indicator to the baseline to yield a difference; and comparing the difference to one or more thresholds to characterize the patient's activity level.

A thirty-sixth non-limiting example is a method as in the thirty-fifth non-limiting example, wherein: the present state indicator is generated by averaging a number, M, of individual samples from the motion sensor; the subtractive baseline is generated by averaging a number, N, of individual samples from the motion sensor; and wherein M is an order of magnitude smaller than N. A thirty-seventh non-limiting example is a method as in either of the thirty-fifth or thirty-sixth non-limiting examples, further comprising: providing a pacing output from the ID to the patient's heart, wherein the pacing output has a rate which is adjustable; and adjusting the pacing output rate in light of the patient's activity level.

A thirty-eighth non-limiting example is a method of operating a motion sensor in an implantable device (ID) for disposition within the heart of a patient, the ID comprising a motion sensor for detecting movement of the patient, the method comprising: instructing a patient having the ID implanted in the heart thereof to adopt a set of postures or engage in a movement; capturing a number of motion sensor outputs while the patient is in one or more postures or engaging in one or more movement while capturing a cardiac electrical signal; identifying a quiet period within the cardiac the cardiac electrical signals during which intrinsic motion of the heart does not impact the output of the motion sensor outputs; and configuring the ID to activate and capture data from the motion sensor during the quiet periods. A thirty-ninth non-limiting example is a method as in the thirty-eighth non-limiting example, wherein the quiet time is defined relative to a predetermined event in the cardiac electrogram. A fortieth non-limiting example is a method comprising repeatedly performing the method of the thirty-eighth non-limiting example using one or more of the following: with and without the patient receiving pacing therapy; and for at least first and second postures or activities.

Each of these non-limiting examples can stand on its own, or can be combined in various permutations or combinations with one or more of the other examples. The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method of operating an implantable device (ID) adapted for disposition within the heart of a patient, the ID comprising a motion sensor for detecting movement of the patient, the method comprising:

initializing the ID by:
  contemporaneously collecting a set of data points from the motion sensor and from a cardiac electrical signal;
  correlating time periods within the set of data points from the motion sensor to cardiac activity reflected by the cardiac electrical signal; and
  configuring the ID to capture data from the motion sensor by reference to specific repeatable elements of the cardiac electrical signal;
using the ID as configured in the initializing step to capture cardiac signals of the patient and motion signals for the patient.

2. The method of claim 1 further comprising;
using the motion signals to determine an activity level of the patient; and
setting and implementing a pacing rate for the patient using the determined activity level.

3. The method of claim 1 wherein the step of configuring the ID to capture data from the motion sensor is performed by:
  determining when intrinsic mechanical motion of the heart is detected by the motion sensor relative to electrical signals of the heart; and
  setting a data capture period for the motion sensor relative to a specified electrical signal of the heart to avoid capturing the intrinsic mechanical motion of the heart with the motion sensor.

4. The method of claim 1 wherein the step of configuring the ID to capture data from the motion sensor is performed by:
  determining when a quiet period in the intrinsic mechanical motion of the heart is detected by the motion sensor relative to electrical signals of the heart; and
  setting a data capture period for the motion sensor relative to a specified electrical signal of the heart to avoid capturing the intrinsic mechanical motion of the heart with the motion sensor.

5. The method of claim 1 wherein the step of configuring the ID to capture data from the motion sensor includes determining a delay after a T-wave in the cardiac electrical signal.

6. The method of claim 5 wherein the delay is configured as a function of cardiac rate.

7. The method of claim 6 wherein the cardiac rate is determined as a rate of pacing output of the ID.

8. The method of claim 6 wherein the cardiac rate is determined as an intrinsic rate of the patient's heart.

9. The method of claim 1 wherein the specific repeatable elements of the cardiac electrical signal are one of an R-wave or a QRS complex.

10. The method of claim 1 wherein the specific repeatable elements of the cardiac electrical signal comprise the T-wave.

11. The method of claim 1 wherein the step of configuring the ID to capture data from the motion sensor by reference to specific repeatable elements of the cardiac electrical signal further includes configuring the ID to maintain the motion sensor in a low power state except when the ID is capturing data therefrom.

12. An implantable medical device (IMD) adapted for implantation within the heart of a patient and comprising:
  a plurality of electrodes adapted for one or more of sensing electrical cardiac activity and delivering therapy;
  a motion sensor for detecting movement of the patient; and
  a processing module configured to receive signals from the motion sensor and from the plurality of electrodes to determine patient status, wherein the processing module is configured to enhance the operation of the device by:
  initializing the IMD by:
    contemporaneously collecting a set of data points from the motion sensor and from a cardiac electrical signal capturing using two or more of the plurality of electrodes;
    correlating time periods within the set of data points from the motion sensor to cardiac activity reflected by the cardiac electrical signal; and
    setting up the IMD to capture data from the motion sensor by reference to specific repeatable elements of the cardiac electrical signal; and
  using the IMD as set up in the initializing step to capture cardiac signals of the patient and motion signals for the patient.

13. An IMD as in claim 12 wherein the processing module is further configured to:
  use the motion signals to determine an activity level of the patient; and
  set and implement a pacing rate for the patient using the determined activity level.

14. An IMD as in claim 12 wherein the processing module is configured to set up the IMD to capture data from the motion sensor by:
  determining when intrinsic mechanical motion of the heart is detected by the motion sensor relative to electrical signals of the heart; and
  setting a data capture period for the motion sensor relative to a specified electrical signal of the heart to avoid capturing intrinsic mechanical motion of the heart with the motion sensor.

15. An IMD as in claim 12 wherein the processing module is configured to set up the IMD to capture data from the motion sensor by:
  determining when a quiet period in the intrinsic mechanical motion of the heart is detected by the motion sensor relative to electrical signals of the heart; and
  setting a data capture period for the motion sensor relative to a specified electrical signal of the heart to avoid capturing intrinsic mechanical motion of the heart with the motion sensor.

16. An IMD as in claim 12 wherein the processing module is configured to set up the IMD to capture data from the motion sensor by determining a delay after a T-wave in the cardiac electrical signal.

17. An IMD as in claim 16 wherein the processing module is configured to set the delay after a T-wave as a function of cardiac rate.

18. An IMD as in claim 12 wherein the specific repeatable elements of the cardiac electrical signal are one of an R-wave or a QRS complex.

19. An IMD as in claim 12 wherein the specific repeatable elements of the cardiac electrical signal comprise the T-wave.

* * * * *